US011773038B2

(12) United States Patent
Luo et al.

(10) Patent No.: US 11,773,038 B2
(45) Date of Patent: Oct. 3, 2023

(54) METHODS FOR OPERATING ACETYLENE HYDROGENATION UNITS IN INTEGRATED STEAM CRACKING AND FLUIDIZED CATALYTIC DEHYDROGENATION SYSTEMS

(71) Applicant: Dow Global Technologies LLC, Midland, MI (US)

(72) Inventors: Lin Luo, Sugar Land, TX (US); Hangyao Wang, Pearland, TX (US); Yu Liu, Lake Jackson, TX (US); Matthew T. Pretz, Lake Jackson, TX (US); Andrzej Malek, Midland, MI (US)

(73) Assignee: Dow Global Technoogies LLC, Midland, MI (US)

( * ) Notice: Subject to any disclaimer, the term of this patent is extended or adjusted under 35 U.S.C. 154(b) by 0 days.

(21) Appl. No.: 17/621,919

(22) PCT Filed: Jun. 8, 2020

(86) PCT No.: PCT/US2020/036586
§ 371 (c)(1),
(2) Date: Dec. 22, 2021

(87) PCT Pub. No.: WO2020/263545

PCT Pub. Date: Dec. 30, 2020

(65) Prior Publication Data

US 2022/0227687 A1    Jul. 21, 2022

Related U.S. Application Data

(60) Provisional application No. 62/865,594, filed on Jun. 24, 2019.

(51) Int. Cl.
*C07C 5/00* (2006.01)
*C07C 5/333* (2006.01)
(Continued)

(52) U.S. Cl.
CPC ............. *C07C 5/3337* (2013.01); *B01J 23/62* (2013.01); *C07C 4/04* (2013.01); *C07C 5/333* (2013.01); *C07C 7/167* (2013.01); *C07C 2523/62* (2013.01)

(58) Field of Classification Search
CPC ............................... C07C 5/3337; C07C 5/48
See application file for complete search history.

(56) References Cited

U.S. PATENT DOCUMENTS 5,847,250 A   12/1998   Flick et al.
8,563,793 B2  10/2013   Zimmerman et al.
(Continued)

FOREIGN PATENT DOCUMENTS

CN      109689600 A      4/2019
WO      2018/024650 A1   2/2018

OTHER PUBLICATIONS

International Search Report and Written Opinion issued by the European Patent Office acting as International Searching Authority for International Patent Application No. PCT/US2020/036586 dated Aug. 28, 2020 (13 total pages).

(Continued)

*Primary Examiner* — Sharon Pregler
(74) *Attorney, Agent, or Firm* — Dinsmore & Shohl LLP

(57) ABSTRACT

A method for operating an acetylene hydrogenation unit in an integrated steam cracking-fluidized catalytic dehydrogenation (FCDh) system may include separating a cracked gas from a steam cracking system and an FCDh effluent from an FCDh system into a hydrogenation feed and an acetylene-depleted stream, the hydrogenation feed comprising at least hydrogen, CO, and acetylene. During normal operating conditions, at least 20% of the CO in the hydrogenation feed is from the cracked gas. The method may include contacting the hydrogenation feed with an acetylene hydrogenation catalyst to hydrogenate at least a portion of the acetylene in (Continued)

the hydrogenation feed to produce a hydrogenated effluent. The steam cracking is operated under conditions that increase CO production such that a concentration of CO in the cracked gas is great enough that when a flowrate of the FCDh effluent is zero, a CO concentration in the hydrogenation feed is at least 100 ppmv.

15 Claims, 5 Drawing Sheets

(51) Int. Cl.
*B01J 23/62* (2006.01)
*C07C 4/04* (2006.01)
*C07C 7/167* (2006.01)

(56) References Cited

U.S. PATENT DOCUMENTS

| | | | |
|---|---|---|---|
| 2014/0249339 | A1 | 9/2014 | Simanzhenkov et al. |
| 2016/0362616 | A1* | 12/2016 | Oprins .................. C10G 49/22 |
| 2019/0161422 | A1 | 5/2019 | Pretz et al. |
| 2021/0371357 | A1 | 12/2021 | Luo et al. |

OTHER PUBLICATIONS

International Search Report/Written Opinion for PCT/US2020/036590 dated Sep. 25, 2020, pp. 1-17.
International Search Report/Written Opinion for PCT/US2020/036582 dated Sep. 25, 2020, pp. 1-16.
Communication Pursuant to Rules 161/162 for Application No. 20735721.1 dated Feb. 3, 2022—pp. 1-3.
Communication Pursuant to Rules 161/162 for Application No. 20750466.3 dated Feb. 3, 2022—pp. 1-3.
Communication Pursuant to Rules 161/162 for Application No. 20750465.5 dated Feb. 11, 2022—pp. 1-3.
International Preliminary Report on Patentability for Application No. PCT/US2020/036590 dated Dec. 28, 2021, pp. 1-11.
International Preliminary Report on Patentability for Application No. PCT/US2020/036586 dated Dec. 28, 2021, pp. 1-11.
International Preliminary Report on Patentability for Application No. PCT/US2020/03682 dated Dec. 28, 2021, pp. 1-10.
Edgar L. Mohundro, "Overview on C2 and C3 Selective Hydrogenation in Ethylene Plants", 15th Ethylene Produces Conference, 2003 AICHE Spring National Meeting, New Orleans, LA.
Chinese Office Action dated Mar. 4, 2023, pertaining to CN Patent Application No. 202080046062.X, 22 pgs.
Hao et al. "Alleviate CO Effect on Front-end Acetylene Converter", Chemical Industry and Engineering Progress, vol. 21, No. 9, 2002, pp. 673-675.

* cited by examiner

METHODS FOR OPERATING ACETYLENE HYDROGENATION UNITS IN INTEGRATED STEAM CRACKING AND FLUIDIZED CATALYTIC DEHYDROGENATION SYSTEMS

CROSS-REFERENCE TO RELATED APPLICATIONS

This application is a National Stage Entry under 35 U.S.C. § 371 of International Patent Application No. PCT/US2020/036586, filed Jun. 8, 2020, which claims priority to U.S. Provisional Patent Application No. 62/865,594, filed on Jun. 24, 2019, the entire disclosures of both of which are hereby incorporated by reference.

BACKGROUND

Field

The present disclosure generally relates to chemical processing systems for producing olefins and the operation thereof and, more specifically, to methods for operating acetylene hydrogenation units in olefin production processes that include fluidized catalytic dehydrogenation (FCDh) process integrated with a steam cracking process.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as such as natural gas condensate or a product stream from a petrochemical operation. For example, hydrocarbon cracking (e.g., steam cracking), catalytic dehydrogenation, and other processes may be used to produce olefins from a hydrocarbon stream. However, hydrocarbon cracking and other processes for producing light olefins can produce byproducts and impurities, such as acetylenic and allenic compounds, which can be poisons to downstream processes and catalysts. Additionally, the presence of high concentrations of acetylene may present a safety concern in downstream processes due to the reactivity of these compounds. Acetylene and other impurities and byproducts can be removed from an olefin-containing hydrocarbon cracking effluent through hydrogenation in a selective hydrogenation process downstream of the hydrocarbon cracking unit. Selective hydrogenation of acetylene compounds in the hydrocarbon cracking effluent can also recover additional product olefins, such as ethylene and propylene.

SUMMARY

In some olefin production processes, light olefins, such as ethylene and propylene for example, may be produced through a combination of steam cracking and fluidized catalytic dehydrogenation (FCDh). Because of the similarities in the composition of the effluents from these processes, a steam cracking system and an FCDh system can be integrated so that the cracked gas from steam cracking system and at least a portion of the FCDh effluent from the FCDh system can be combined and processed in a common effluent processing system downstream of the steam cracking system and FCDh system. The effluent processing system may include separation and purification systems to isolate product streams and remove unwanted contaminants and reaction byproducts. The common effluent processing system may include an acetylene hydrogenation unit operable for hydrogenating acetylene produced in the steam cracking unit.

The acetylene hydrogenation unit can be sensitive to the concentration of carbon monoxide (CO) in the feed to the acetylene hydrogenation unit. Not intending to be limited by any particular theory, it is believed that CO interacts with the hydrogenation catalyst in the acetylene hydrogenation unit to decrease the activity of the hydrogenation catalyst for hydrogenating acetylene. Conversely, decreasing the CO concentration in the acetylene hydrogenation unit may increase the activity of the hydrogenation catalyst. A sudden decrease in the CO concentration in the hydrogenation feed to the acetylene hydrogenation unit may increase the activity of the hydrogenation catalyst, which can lead to increased hydrogenation of olefin products in the hydrogenation feed, such as ethylene and propylene, and reduced olefin selectivity. Rapid increases in hydrogenation of olefins, such as ethylene and propylene, may lead to thermal runaway of the acetylene hydrogenation unit due to rapid heat release from the olefin hydrogenation reactions, which are exothermic.

The FCDh effluent from the FCDh process generally may have a greater concentration of CO than the concentration of CO in the cracked gas from the steam cracking unit. Therefore, when an integrated process for producing olefins is operating with both the cracked gas and at least a portion of the FCDh effluent passed to the effluent processing system, the concentration of CO in the feed to the acetylene hydrogenation unit may be substantially greater than the concentration of CO from the cracked gas only. A discontinuity in operation of the FCDh system, such as during an unexpected FCDh trip, may cause a sudden decrease in or complete loss of flow of the FCDh effluent to the effluent processing system. This can result in a sudden and significant decrease in the CO concentration of the hydrogenation feed. As previously discussed, a reduction in the CO concentration may lead to thermal runaway of the acetylene hydrogenation unit due to the increased hydrogenation of olefin products and the generation of heat from the exothermic hydrogenation reaction. Thus, a decrease in or complete loss of flow of the FCDh effluent to the effluent processing system may lead to thermal runaway of the acetylene hydrogenation reactor. The decrease or loss of the flow of FCDh effluent to the effluent processing system may also decrease the total flow rate of reactants through the acetylene hydrogenation unit, resulting in smaller Gas Hourly Space Velocity (GHSV) or longer residence time for the hydrogenation feed, which may also increase the conversion olefins leading to thermal runaway. The increased temperatures in excess of 200° C. experienced during thermal runaway can trip the acetylene hydrogenation unit, requiring restart of the system. Additionally, the increased temperatures in excess of 200° C. can damage the hydrogenation catalyst and equipment, such as reactors, instruments, heat exchangers, and other equipment, and may increase safety risks. In many runaway situations, severe loss of catalyst performance resulting from thermal runaway can require catalyst replacement which leads to significant unit down time. Thermal runaway can also result in increased loss of olefin products through over-hydrogenation of the ethylene and propylene.

The methods disclosed herein may reduce or prevent thermal runaway of the acetylene hydrogenation unit of an integrated process for producing olefins that combines a cracked gas from a steam cracking system and at least a portion of an FCDh effluent from an FCDh system. In particular, the methods disclosed herein reduce or prevent thermal runaway of the acetylene hydrogenation unit during a decrease in or complete loss of flow of the FCDh effluent to the effluent processing system by operating the steam cracking unit of the steam cracking system to increase the concentration of CO in the cracked gas. Increasing the amount of CO in the cracked gas may prevent or reduce thermal runaway in the acetylene hydrogenation unit by increasing the proportion of CO in the hydrogenation feed contributed by the steam cracking system, thereby reducing the proportion of CO in the hydrogenation feed contributed by the FCDh effluent. Reducing the proportion of CO in the hydrogenation feed contributed by the FCDh effluent may reduce the impact of instant increase of catalyst activity and fast loss of selectivity of the acetylene hydrogenation unit caused by a sudden decrease in or complete loss of the flow of the FCDh effluent to the effluent processing system. The methods disclosed herein may reduce the probability of thermal runaway in the event that the FCDh system suddenly stops, thus reducing or preventing thermal damage to equipment and catalysts and reducing or preventing over-hydrogenation and loss of valuable olefin products produced in the steam cracking and FCDh systems.

According to one embodiment presently described, a method for operating an acetylene hydrogenation unit in an integrated steam cracking-fluidized catalytic dehydrogenation (FCDh) system may include cracking at least a portion of a first hydrocarbon feed in a steam cracking system to produce a cracked gas comprising at least hydrogen, carbon monoxide (CO), and acetylene, dehydrogenating at least a portion of a second hydrocarbon feed in an FCDh system to produce an FCDh effluent comprising at least hydrogen and CO, and separating the cracked gas and at least a portion of the FCDh effluent into a hydrogenation feed and an acetylene-depleted stream. The hydrogenation feed may include at least hydrogen, CO, and acetylene. The hydrogenation feed may include at least 95% of the CO from the cracked gas and the FCDh effluent. During normal operating conditions, at least 20% of the CO in the hydrogenation feed may be from the cracked gas. The method may further include contacting the hydrogenation feed with an acetylene hydrogenation catalyst in an acetylene hydrogenation unit. The contacting may cause hydrogenation of at least a portion of the acetylene in the hydrogenation feed to produce a hydrogenated effluent. The steam cracking system may be operated under conditions that increase CO production such that a concentration of CO in the cracked gas may be great enough that when a flowrate of the FCDh effluent is zero, a CO concentration in the hydrogenation feed is at least 100 ppmv.

In one or more embodiments, operating the steam cracking system under conditions that increase CO production such that the concentration of CO in the cracked gas is great enough that when the flowrate of the FCDh effluent is zero, the CO concentration in the hydrogenation feed is at least 100 ppmv, may reduce or prevent thermal runaway of the acetylene hydrogenation unit in response to a disruption in the flow of the FCDh effluent to the acetylene hydrogenation unit.

In one or more other embodiments, the concentration of CO in the cracked gas may be great enough that when the flowrate of the FCDh effluent is zero, the CO concentration in the hydrogenation feed may be from 100 ppmv to 450 ppmv.

In one or more embodiments, maintaining the amount of the CO from the cracked gas in the hydrogenation feed greater than or equal to 20% by mass of the total amount of CO in the hydrogenation feed may reduce or prevent thermal runaway of the acetylene hydrogenation unit in response to a disruption in flow of the FCDh effluent to the acetylene hydrogenation unit.

In one or more embodiments the steam cracking system may be operated under conditions that increase CO production by modifying an amount of sulfur-containing compounds, methanol, or both, introduced to the steam cracking system. The sulfur-containing compounds may include at least one of dimethyl disulfide (DMDS), dimethyl sulfide (DMS), diethyl disulfide (DEDS), methyl mercaptan (MM), or combinations thereof.

In one or more embodiments, the method may further include increasing a temperature of the hydrogenation feed in response to increasing an amount of CO in the cracked gas to maintain a concentration of acetylene in the hydrogenated effluent less than a target acetylene concentration.

In some embodiments, the acetylene hydrogenation unit may include at least a first hydrogenation reactor and a second hydrogenation reactor downstream of the first hydrogenation reactor. Maintaining the amount of CO from the cracked gas in the hydrogenation feed greater than or equal to 20% of the total amount of CO in the hydrogenation feed may maintain a conversion of acetylene in the first hydrogenation reactor greater than or equal to 80% in response to a decrease in the flow of the FCDh effluent to the acetylene hydrogenation unit.

In one or more embodiment, in response to a decrease in flow of the at least a portion of the FCDh effluent to the separator, an absolute value of a change in a Delta T of a first hydrogenation reactor of the acetylene hydrogenation unit may be less than 10° C. The Delta T of the first hydrogenation reactor may be a difference between an inlet temperature and an outlet temperature of the first hydrogenation reactor.

In some embodiments, a flow ratio may be less than or equal to 1/2. The flow ratio may be the mass flow rate of the portion of the FCDh effluent passed to the separation system divided by the mass flow rate of the portion of the cracked gas in the hydrogenation feed.

In some embodiments, the hydrogenation feed may include methyl acetylene, propadiene, and at least one cracker product, the at least one cracker product comprising one or more of ethylene, propylene, methane, ethane, propane, or combinations of these.

In some embodiments, the hydrogenated effluent may have a concentration of acetylene of less than or equal to 2 ppm by volume.

In some embodiments, the FCDh effluent may include at least one FCDh product, wherein the at least one FCDh product comprises ethylene, propylene, or both.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
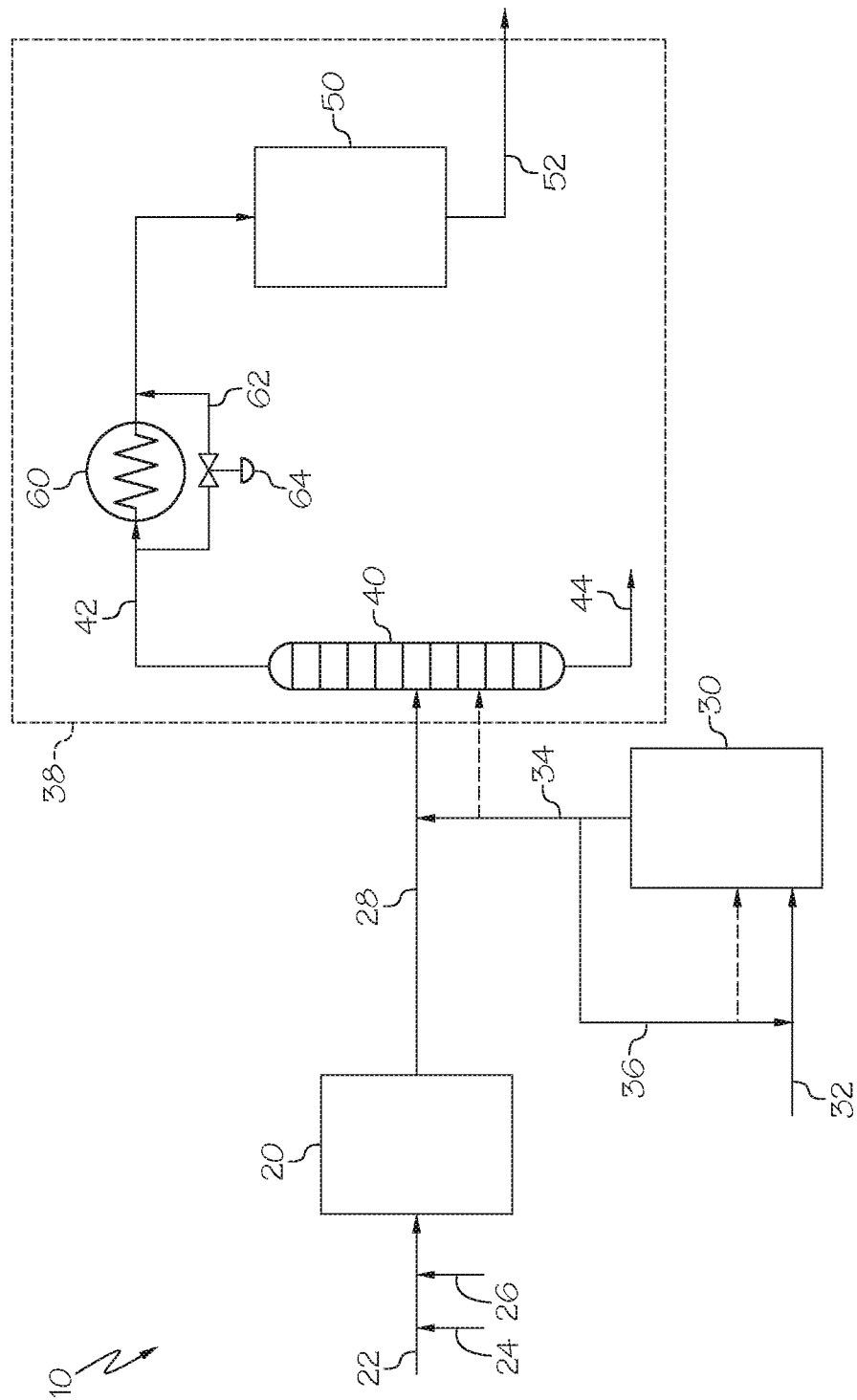
FIG. 1 schematically depicts an integrated process for producing olefins that includes an FCDh system integrated with a steam cracking system and a shared effluent processing system, according to one or more embodiments shown and described herein.

It should be understood that the drawings are schematic in nature, and may not include some components of reactor systems commonly employed in the art, such as, without limitation, sensors, temperature transmitters, pressure transmitters, flow meters, pumps, valves, heat exchangers, internal reactor structures, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

One or more embodiments of the present disclosure are directed to methods for operating an acetylene hydrogenation unit in an integrated process for producing olefins. In particular, one or more embodiments of the present disclosure are directed to methods for operating the acetylene hydrogenation unit of the olefin production process to reduce or prevent thermal runaway of the acetylene hydrogenation unit in the event of a sudden decrease and/or loss of flow of the FCDh effluent to the effluent processing system. In some embodiments of the present disclosure, the methods for operating an acetylene hydrogenation unit in an integrated steam cracking-fluidized catalytic dehydrogenation (FCDh) system include cracking at least a portion of a first hydrocarbon feed in a steam cracking system to produce a cracked gas comprising at least hydrogen, carbon monoxide (CO), and acetylene, and dehydrogenating at least a portion of a second hydrocarbon feed in an FCDh system to produce an FCDh effluent comprising at least hydrogen and CO. The methods may further include separating the cracked gas and at least a portion of the FCDh effluent into a hydrogenation feed and an acetylene-depleted stream, the hydrogenation feed comprising at least hydrogen, CO, and acetylene. The hydrogenation feed may include at least 99% of the CO from the cracked gas and the FCDh effluent. During normal operating conditions, at least 20% of the CO in the hydrogenation feed is from the cracked gas. The methods may further include contacting the hydrogenation feed with an acetylene hydrogenation catalyst in an acetylene hydrogenation unit, the contacting causing hydrogenation of at least a portion of the acetylene in the hydrogenation feed to produce a hydrogenated effluent. The steam cracking system may be operated under conditions that increase CO production such that a concentration of CO in the cracked gas is great enough that when a flowrate of the FCDh effluent is zero, a CO concentration in the hydrogenation feed is at least 100 ppmv. The increased CO in the cracked gas may reduce the degree of activity increase for the acetylene hydrogenation unit in response to a reduction or complete loss of flow of the FCDh effluent to the separation system, thereby reducing or preventing thermal runaway of the acetylene hydrogenation unit.

Described herein is an example of an integrated process for producing olefins by steam cracking combined with FCDh and utilizing a common acetylene hydrogenation unit. The integrated process is utilized to provide context for the methods of operating the acetylene hydrogenation unit presently disclosed, which may reduce or prevent breakthrough of acetylene to downstream processes. It should be understood that the schematic diagrams of FIGS. 1-4 are only example systems, and that other systems suitable for producing olefins are contemplated herein, and the concepts described herein may be utilized in such alternate systems. For example, the concepts described herein may be equally applied to other systems with alternate reactor units and regeneration units, such as those that operate under non-fluidized conditions or are downers rather than risers. Additionally, the presently described methods and processes for processing a chemical stream in a reactor system should not be limited only to embodiments for reactor systems designed to produce light olefins or alkyl aromatics through steam cracking integrated with fluidized catalytic dehydrogenation, such as the reactor system described with respect to FIG. 1, as other processes for producing olefins (e.g., utilizing different feedstocks) are contemplated.

The reactor systems and methods for processing the chemical streams will now be discussed in further detail with reference to FIG. 1. The chemical stream that is processed may be referred to as a feed stream or simply a feed, which is processed by a reaction, separation, or other process to form a product stream, reactor effluent, or just effluent. The feed may comprise a composition, and depending upon the feed composition, an appropriate catalyst may be utilized to convert the contents of the feed into an effluent that may include light olefins or other chemical products.

As used herein, "start-up" may generally refer to the time when reactor temperature, reactor pressure, flow rates (e.g., flow rates of feed gas to the reactor (hydrocarbon and/or inert gases), fuel gas and air for catalyst regeneration, gas for catalyst stripping and fluidization, oxygen-containing gas for oxygen treating the catalyst, etc.), catalyst recirculation rates, or combinations of these are being established but have not yet reached the desired values for stable operation for the given reaction.

As used herein, "shut-down" may generally refer to the time when the temperatures, pressures, flow rates, and/or catalyst recirculation rates of the reactor system (e.g., reactor and/or regenerator) are being reduced prior to the end of the process reaction.

System recycle may refer to operation of a reactor system in which at least a portion of the reactor effluent (e.g., FCDh effluent) may be recycled back to the hydrocarbon feed or directly back to the reactor. System recycle events may include off-spec products events in which the reactor system is operated in a system recycle mode until the reactor effluent and/or operating conditions of the reactor are returned back to target or normal operating conditions. The reactor system may also be operated in system recycle mode in response to planned or unplanned interruptions in operation of other reactor systems, such as disruptions in operation of the steam cracking system, integrated with the reactor system disclosed herein. In some embodiments, system recycle may result in the temperature of the reactor decreasing to a low temperature (i.e., <550° C.). In other circumstances, system recycle may include circulating an inert gas through the reactor to maintain the catalyst in a fluidized state.

Unit trip may refer to conditions when a reactor unit completely shuts down, or conditions in which temperatures are reduced, and/or flow rates of one or more streams are reduced or bypassed due to, for example, runaway conditions during chemical processing. Unit trip may include different levels of unit trips, such as severe unit trips in which the entire reactor system is completely shutdown, or a mid-level trip in which the temperature is reduced, the pressure is reduced, or one or more streams are bypassed. Low-temperature reaction conditions, such as those present during start-up, shut-down, system recycle, or unit trip and conditions in which inert gases are circulated through the reactor system without hydrocarbon feed streams may be referred to as non-normal operating conditions herein. Normal operating conditions refer to high temperature, steady state conditions such as temperatures above 550° C. or those suitable for catalytic reaction of a given reactant.

As used herein, the term "hydrogenation feed" refers to an effluent from the separation system passed to the acetylene hydrogenation unit that includes at least 95% by mass of the acetylene from the cracked gas introduced to the separation system.

As used herein, the term "acetylene-depleted stream" refers to another effluent stream from the separation system that is different than the hydrogenation feed and includes less than 5% by mass of the acetylene from the cracked gas passed to the separation system.

As used herein, the terms "upstream" and "downstream" are relative to the direction of flow of materials through the integrated process. For example, a first unit operation is upstream of a second unit operation if one or more material streams flow from the first unit operation to the second unit operation. The first unit operation is downstream of the second unit operation if one or more material streams flow from the second unit operation to the first unit operation.

As used herein, the term "selectivity" may refer to a ratio of the moles of a desired product to moles of all the products in a reactor effluent with all the products normalized to the same carbon number. For example, ethylene selectivity of the acetylene hydrogenation unit may be a ratio of the moles of additionally produced ethylene in the hydrogenated effluent divided by the total moles of all the products produced during the hydrogenation reaction. For example, if all acetylene is converted to ethylene, the selectivity is 100%. If all acetylene is converted to ethane, the selectivity is 0 (zero). If all the acetylene and also some of incoming ethylene is converted to ethane, the selectivity then becomes negative.

As used herein, the term "breakthrough" may refer to passing of a specific reactant, such as but not limited to, acetylene, methyl acetylene, propadiene, or other compound, from one processing unit to another downstream processing unit in an amount greater than a threshold value specified by the olefin users, for example 2 parts per million by volume (ppmv). In an example, breakthrough may occur when the specific reactant undergoes substantially incomplete conversion in a reaction system so that an effluent passed out of the reaction system has a concentration of the specific reactant of greater than 2 ppmv, or greater than 1 ppmv depending on olefin users and the location.

As used herein, the term "threshold acetylene concentration" may refer to a concentration of acetylene in a hydrogenated effluent from the acetylene hydrogenation unit at or below which the concentration of acetylene is considered to be within the specifications for product purity provided by olefin users and/or does not cause fouling of catalysts or other disruptions in downstream processes.

As used herein, the term "thermal runaway" may refer to a condition of a process in which an incremental increase in temperature of the process changes the operating conditions in a manner that produces or generates heat, which further increases the temperature.

As used herein, the term "normal operating conditions" may refer to high temperature, steady state conditions such as temperatures suitable for catalytic reaction of a given reaction, such as a temperature suitable for conducting the acetylene hydrogenation reaction in the acetylene hydrogenation unit.

Referring to FIG. 1, an integrated process 10 for producing olefins is schematically depicted. The integrated process 10 may include a steam cracking system 20, a fluidized catalytic cracking (FCDh) system 30, and an effluent processing system 38, which may be operable to process the product effluents from the steam cracking system 20 and the FCDh system 30. The steam cracking system 20 may be operable to convert at least a portion of a first hydrocarbon feed 22 to produce a cracked gas 28 that includes at least hydrogen, carbon monoxide (CO), acetylene, and at least one steam cracker product. The FCDh system 30 may be operable to convert at least a portion of a second hydrocarbon feed 32 to produce an FCDh effluent 34 that includes at least hydrogen, CO, and at least one FCDh product. The cracked gas 28, or the cracked gas 28 and at least a portion of the FCDh effluent 34, may be passed to the effluent processing system 38, which may be operable to process the cracked gas 28 and/or the FCDh effluent 34 to produce one or more product streams (not shown). The effluent processing system 38 may include at least a separation system 40, an acetylene hydrogenation unit 50 downstream of the separation system 40, and a heat exchanger 60 disposed between the separation system 40 and the acetylene hydrogenation unit 50. The effluent processing system 38 may include additional separation and/or purification processes (not shown) disposed downstream of the acetylene hydrogenation unit 50.

Figure 2:
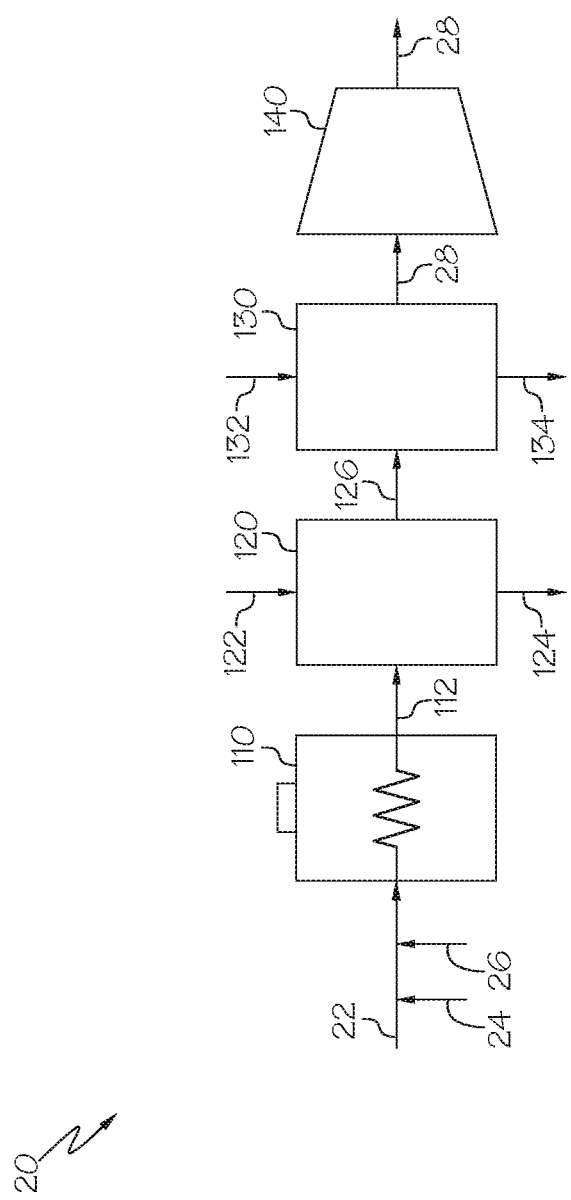
FIG. 2 schematically depicts the steam cracking system of the integrated process of FIG. 1, according to one or more embodiments shown and described herein.

Referring to FIG. 2, an embodiment of a steam cracking system 20 is schematically depicted. The steam cracking system 20 may include a steam cracking unit 110 and one or more of an oil quench unit 120, a water quench unit 130, a compressor system 140, or combinations of these. In some embodiments, the steam cracking system 20 may also include an acid gas removal unit (not shown). The first hydrocarbon feed 22 may be introduced to the steam cracking unit 110 for cracking one or more hydrocarbon constituents of the first hydrocarbon feed 22 to produce one or more olefins. The first hydrocarbon feed 22 may be any hydrocarbon stream, such as a product stream from a petrochemical process or a refining operation for crude oil, shale gas, or other hydrocarbon sources. In some embodiments, the first hydrocarbon feed 22 may include a plurality of different hydrocarbon streams combined prior to or in the steam cracking unit 110. In some embodiments, the first hydrocarbon feed 22 may be a light hydrocarbon feedstock, such as a feedstock including ethane, propane, butane, naphtha, other light hydrocarbon, or combinations of these.

The steam cracking unit 110 may be operable to receive the first hydrocarbon feed 22 and crack one or more constituents of the first hydrocarbon feed 22 to produce a cracker effluent 112. The steam cracking unit 110 may be operable to contact the first hydrocarbon feed 22 with steam at temperatures of from 500° C. to 850° C. to produce the cracker effluent 112. A sulfur-containing composition 24, a methanol-containing stream 26, or both, may also be introduced to the steam cracking unit 110. The sulfur-containing composition 24, the methanol-containing stream 26, or both, may be introduced directly into the steam cracking unit 110 or may be combined with the first hydrocarbon feed 22 upstream of the steam cracking unit 110. The sulfur-containing composition 24 may include one or more sulfur-containing compounds, such as, but not limited to dimethyl disulfide (DMDS), dimethyl sulfide (DMS), diethyl disulfide (DEDS), methyl mercaptan (MM), or combinations thereof. The sulfur-containing compounds from the sulfur-containing composition 24 may passivate the heating coil in the steam cracking furnace of the steam cracking unit 110 to manage the formation of coke in the steam cracking unit 110. Increasing or decreasing the sulfur-containing compounds may change an amount of CO generated in the steam cracking unit 110, thereby changing the CO concentration (e.g., amount of CO) in the cracker effluent 112.

Ethane, propane, naphtha, and other hydrocarbons present in the first hydrocarbon feed 22 may be steam cracked in the steam cracking unit 110 to produce at least one or more light olefins, such as but not limited to ethylene, propylene, butenes, or combinations of these. The steam cracking unit 110 may be operated under conditions (i.e., temperature, pressure, residence time, etc.) sufficient to produce one or more light olefins, such as ethylene and propylene, from the hydrocarbons in the first hydrocarbon feed 22. In some embodiments, the steam cracking unit 110 may be operated at a temperature of from 500° C., to 850° C., from 500° C. to 810° C., from 550° C. to 850° C., from 550° C. to 810° C., from 600° C. to 850° C., or from 600° C. to 810° C. The temperature of the steam cracking unit 110 may depend on the composition of the first hydrocarbon feed 22 introduced to the steam cracking unit 110. Other suitable operating conditions for hydrocarbon cracking processes are well known in the art.

The cracker effluent 112 may include one or more cracking reaction products, such as, but not limited to, ethylene, propylene, butenes (e.g., 1-butene, trans-2-butene, cis-2-butene, isobutene), ethane, propane, other light hydrocarbons, or combinations of these. The cracker effluent 112 can also include hydrogen, CO, acetylene, methyl acetylene, propadiene, methane, other compounds produced in the steam cracking unit 110, unreacted constituents of the first hydrocarbon feed 22, or combinations of these. For example, the cracking reactions in the steam cracking unit 110 may produce byproducts, such as hydrogen and CO, and side-reaction products, such as acetylene, methyl acetylene, propadiene, other side-reaction products, or combinations of these. Additionally, unreacted hydrocarbons and/or other constituents of the first hydrocarbon feed 22 may pass through the steam cracking unit 110 without undergoing reaction so that the cracker effluent 112 includes these unreacted constituents of the first hydrocarbon feed 22. Acid and alcohol gases may also be produced in the steam cracking unit 110.

Referring still to FIG. 2, the cracker effluent 112 may be passed from the steam cracking unit 110 to the oil quench unit 120 downstream of the steam cracking unit 110. The oil quench unit 120 maybe operable to quench the cracker effluent 112 with a hydrocarbon quench liquid 122 to reduce the temperature of the cracker effluent 112 and remove heavy hydrocarbon constituents to produce an oil-quench effluent 126. The oil-quench effluent 126 may be passed from the oil quench unit 120 to the water quench unit 130 downstream of the oil quench unit 120. The water quench unit 130 maybe operable to quench the cracker effluent 112 with liquid water to further reduce the temperature of the oil-quench effluent 126 and remove steam to produce the cracked gas 28. Although the water quench unit 130 is shown in FIG. 2 as being downstream of the oil quench unit 120, it is understood that the water quench unit 130 may alternatively be positioned upstream of the oil quench unit 120. The steam cracking system 20 may optionally include an acid gas removal system (not shown) for removing acid gases from the cracked gas 28. Alternatively, in some embodiments, the acid gas removal system may be incorporated into the effluent processing system 38 (FIG. 1). The cracked gas 28 may be passed to a compression system 140 operable to reduce the volume of the cracked gas 28 upstream of the effluent processing system 38.

Figure 3:
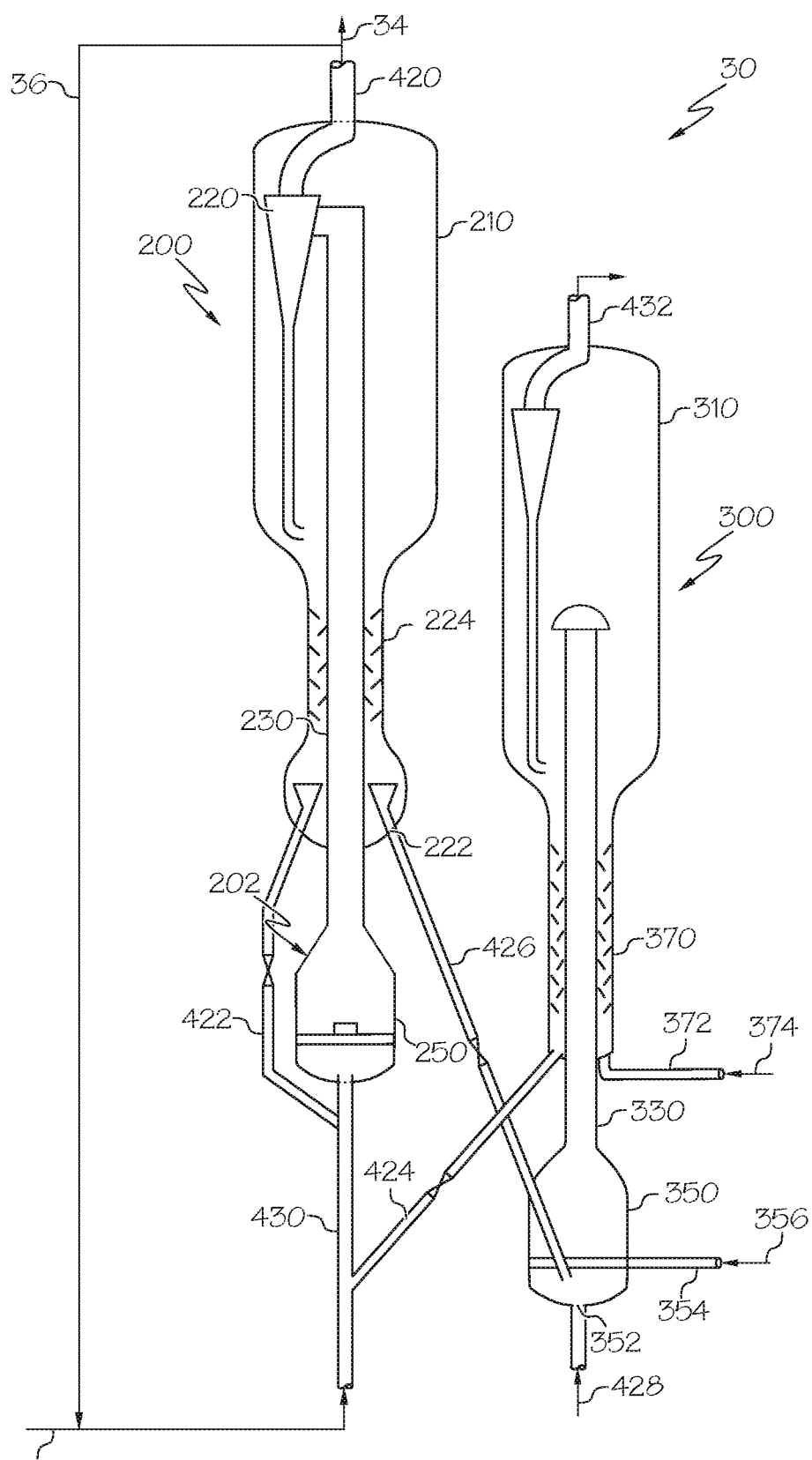
FIG. 3 schematically depicts the FCDh system of the integrated process of FIG. 1, according to one or more embodiments shown and described herein.

Referring now to FIG. 3, the FCDh system 30 may be operable to receive a second hydrocarbon feed 32 and contact the second hydrocarbon feed 32 with a dehydrogenation catalyst to produce an FCDh effluent 34. The second hydrocarbon feed 32 to the FCDh system 30 may include at least one of propane, n-butane, iso-butane, ethane, or ethylbenzene. The second hydrocarbon feed 32 may include one or more hydrocarbon streams from a hydrocarbon processing facility. The second hydrocarbon feed 32 may be the same as or different than the first hydrocarbon feed 22. In some embodiments, the second hydrocarbon feed 32 may include a propane or ethane stream recovered from the effluent processing system 38 and recycled back to the FCDh system 30. In the FCDh system 30, at least a portion of the second hydrocarbon feed 32 may be converted to light olefins or other products through dehydrogenation in the presence of a dehydrogenation catalyst. The dehydrogenation catalyst may be any catalyst known in the art for dehydrogenating hydrocarbons to produce olefins. The FCDh effluent 34 may include at least CO, hydrogen, and at least one FCDh product. The at least one FCDh product may include one or more of ethylene, propylene, or combinations thereof.

Referring to FIG. 3, an example FCDh system 30 is schematically depicted. The FCDh system 30 may include a reactor portion 200 and a catalyst processing portion 300. As used herein in the context of FIG. 1, the reactor portion 200 may refer to a portion of the FCDh system 30 in which the major process reaction takes place. For example, the second hydrocarbon feed 32 may be dehydrogenated in the presence of the dehydrogenation catalyst in the reactor portion 200 of the FCDh system 30. The reactor portion 200 comprises a reactor 202 which may include a downstream reactor section 230, an upstream reactor section 250, and a catalyst separation section 210, which serves to separate the catalyst from the chemical products formed in the reactor 202.

Also, as used herein, the catalyst processing portion 300 of the FCDh system 30 of FIG. 3 generally refers to the portion of the FCDh system 30 in which the catalyst is in some way processed, such as removal of coke deposits, heating of the catalyst, reactivating the catalyst, other processing operations, or combinations of these, during normal operation of the FCDh system 30. In some embodiments, the catalyst processing portion 300 may include a combustor 350, a riser 330, a catalyst separation section 310, and an oxygen treatment zone 370. The combustor 350 of the catalyst processing portion 300 may include one or more lower combustor inlet ports 352 and may be in fluid communication with the riser 330. The combustor 350 may be in fluid communication with the catalyst separation section 210 via transfer line 426, which may supply deactivated catalyst (during normal operating conditions) from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via transfer line 424 and transport riser 430), which may supply processed catalyst from the catalyst processing portion 300 back to the reactor portion 200. The combustor 350 may include the lower combustor inlet port 352 where air inlet 428 connects to the combustor 350. The air inlet 428 may supply air or other reactive gases, such as an oxygen-containing gas to the combustor 350. Air and/or other reactive gases, may be introduced to the combustor 350 to aid in combustion of a supplemental fuel. The combustor 350 may also include a fuel inlet 354. The fuel inlet 354 may supply a fuel, such as a hydrocarbon stream 356 to the combustor 350. The oxygen treatment zone 370 may include an oxygen-containing gas inlet 372, which may supply an oxygen-containing gas 374 to the oxygen treatment zone 370 for oxygen treatment of the catalyst.

Referring to FIG. 3, general operation of the FCDh system 30 to conduct a continuous reaction under normal operating conditions will be described. During operation of the reactor portion 200 of the FCDh system 30, the second hydrocarbon feed 32 may enter the transport riser 430, and FCDh effluent 34 may exit the FCDh system 30 via pipe 420. According to one or more embodiments, the FCDh system 30 may be operated by feeding the second hydrocarbon feed 32 and a fluidized dehydrogenation catalyst into the upstream reactor section 250. Hydrocarbons in the second hydrocarbon feed 32 may contact the dehydrogenation catalyst in the upstream reactor section 250, and each may flow upwardly into and through the downstream reactor section 230 to produce at least one FCDh product under normal operating conditions.

The FCDh effluent 34 and the dehydrogenation catalyst may be passed out of the downstream reactor section 230 to a separation device 220 in the catalyst separation section 210. The FCDh effluent 34 may include hydrogen, CO, and at least one FCDh product. The FCDh effluent 34 may also include unreacted portions of the second hydrocarbon feed 32, fluidization gases, byproducts, reaction intermediates, other gases, or combinations of these. The at least one FCDh product may include ethylene, propylene, or other light olefins. The FCDh effluent 34 may have a CO concentration greater than the concentration of CO in the cracked gas 28 from the steam cracking system 20. The FCDh effluent 34 may have a concentration of CO of from 600 parts per million by volume (ppmv) to 2400 ppmv, such as from 1000 ppmv to 2000 ppmv.

The dehydrogenation catalyst may be separated from the FCDh effluent 34 in the separation device 220. The FCDh effluent 34 may then be transported out of the catalyst separation section 210. For example, the separated vapors of the FCDh effluent 34 may be removed from the FCDh system 30 via a pipe 420 at a gas outlet port of the catalyst separation section 210. In some embodiments, the separation device 220 may be a cyclonic separation system, which may include two or more stages of cyclonic separation.

According to some embodiments, following separation from vapors of the FCDh effluent 34 in the separation device 220, the dehydrogenation catalyst may generally move through the stripper 224 to the reactor catalyst outlet port 222 where the dehydrogenation catalyst may be transferred out of the reactor portion 200 via transfer line 426 and into the catalyst processing portion 300. Optionally, the dehydrogenation catalyst may also be transferred directly back into the upstream reactor section 250 via standpipe 422. In some embodiments, recycled dehydrogenation catalyst from the stripper 224 may be premixed with processed dehydrogenation catalyst from the catalyst processing portion 300 in the transport riser 430.

The separated dehydrogenation catalyst may be passed from the catalyst separation section 210 to the combustor 350 of the catalyst processing portion 300. The dehydrogenation catalyst may be processed in the catalyst processing portion 300 during normal operation to remove coke deposits, heat the catalyst, reactivate the catalyst, other catalyst processing, or any combinations of these. As previously discussed, processing the dehydrogenation catalyst in the catalyst processing portion 300 may include removing coke deposits from the catalyst, raising the temperature of the catalyst through combustion of a combustion fuel source, reactivating the catalyst, stripping one or more constituents from the catalyst, other processing operation, or combinations of these. In some embodiments, processing the dehydrogenation catalyst in the processing portion 300 may include combusting a combustion fuel source in the presence of the dehydrogenation catalyst in the combustor 350 to remove coke deposits and/or heat the dehydrogenation catalyst to produce a heated catalyst. The heated dehydrogenation catalyst may be separated from the combustion gases in the catalyst separation section 310.

In some embodiments, the heated dehydrogenation catalyst may then be reactivated by conducting an oxygen treatment of the heated dehydrogenation catalyst. The oxygen treatment may include exposing the heated dehydrogenation catalyst to an oxygen-containing gas 374 for a period of time sufficient to reactivate the dehydrogenation catalyst. The oxygen treatment to reactivate the dehydrogenation catalyst may be conducted after combustion of the supplemental fuel to heat the dehydrogenation catalyst. The oxygen treatment may include treating the heated dehydrogenation catalyst with the oxygen-containing gas 374 for a period of at least two minutes, which may reactivate the dehydrogenation catalyst to produce a reactivated dehydrogenation catalyst. The oxygen-containing gas 374 may include an oxygen content of from 5 mole % to 100 mole % based on total molar flow rate of the oxygen-containing gas 374. In some embodiments, the oxygen treatment of the dehydrogenation catalyst may include maintaining the dehydrogenation catalyst at a temperature of at least 660° C. while exposing the dehydrogenation catalyst to a flow of the oxygen-containing gas 374 for a period of time greater than two minutes and sufficient to produce a reactivated dehydrogenation catalyst having a catalytic activity that is greater than the heated dehydrogenation catalyst after being heated by combustion of the supplemental fuel. The oxygen treatment may be conducted in the oxygen treatment zone 370, which may be downstream of the catalyst separation section 310 of the catalyst processing portion 300.

The combustion gases from combustion of coke and/or the supplemental fuel during processing of the dehydrogenation catalyst or other gases introduced to the dehydrogenation catalyst during catalyst processing and catalyst reactivation may be removed from the catalyst processing portion 300 via a regenerator effluent outlet 432.

FIG. 3 and the preceding discussion present one embodiment of a system for catalytically dehydrogenating hydrocarbons to produce light olefins. However, it is understood that other reactor system configurations may be employed for catalytic dehydrogenation of hydrocarbons to produce light olefins without departing from the scope of the present disclosure. For example, in some embodiments, the FCDh system 30 may include any type of fluidized reactor system operable to contact the second hydrocarbon feed 32 with a catalyst in a fluidization regime, such as bubbling regime, slug flow regime, turbulent regime, fast fluidization regime, pneumatic conveying regime, or combinations thereof.

Referring again to FIG. 3, the FCDh system 30 may be operated in system recycle in which at least a portion of the FCDh effluent 34 is recycled back to the reactor portion 200 of the FCDh system 30. The FCDh system 30 may be operated in system recycle mode during start-up of the FCDh system 30 or in response to an off-spec event in which the composition of the FCDh effluent 34 does not conform to the product stream target standards. In these situations, the FCDh effluent 34 may be recycled back to the FCDh system 30 while adjustments are made to the FCDh system 30 to bring the composition of the FCDh effluent 34 back into conformance. System recycle may also occur when the reactor system is integrated with another reactor system (e.g., such as the steam cracking system 20) and the other reactor system experiences an interruption (e.g., planned events such as planned maintenance or unplanned events such unexpected failures of equipment such as furnace, compressors, or other equipment). During system recycle operation, at least a portion of or all of the FCDh effluent 34 may be recycled back to the FCDh system 30 in an FCDh effluent recycle 36. The FCDh effluent recycle 36 may be combined with the second hydrocarbon feed 32 upstream of the transport riser 430 as shown in FIG. 3. In some embodiments, the FCDh effluent recycle 36 may be passed directly to the transport riser 430, in which the FCDh effluent recycle 36 is then combined with the second hydrocarbon feed 32 and the dehydrogenation catalyst.

Figure 4:
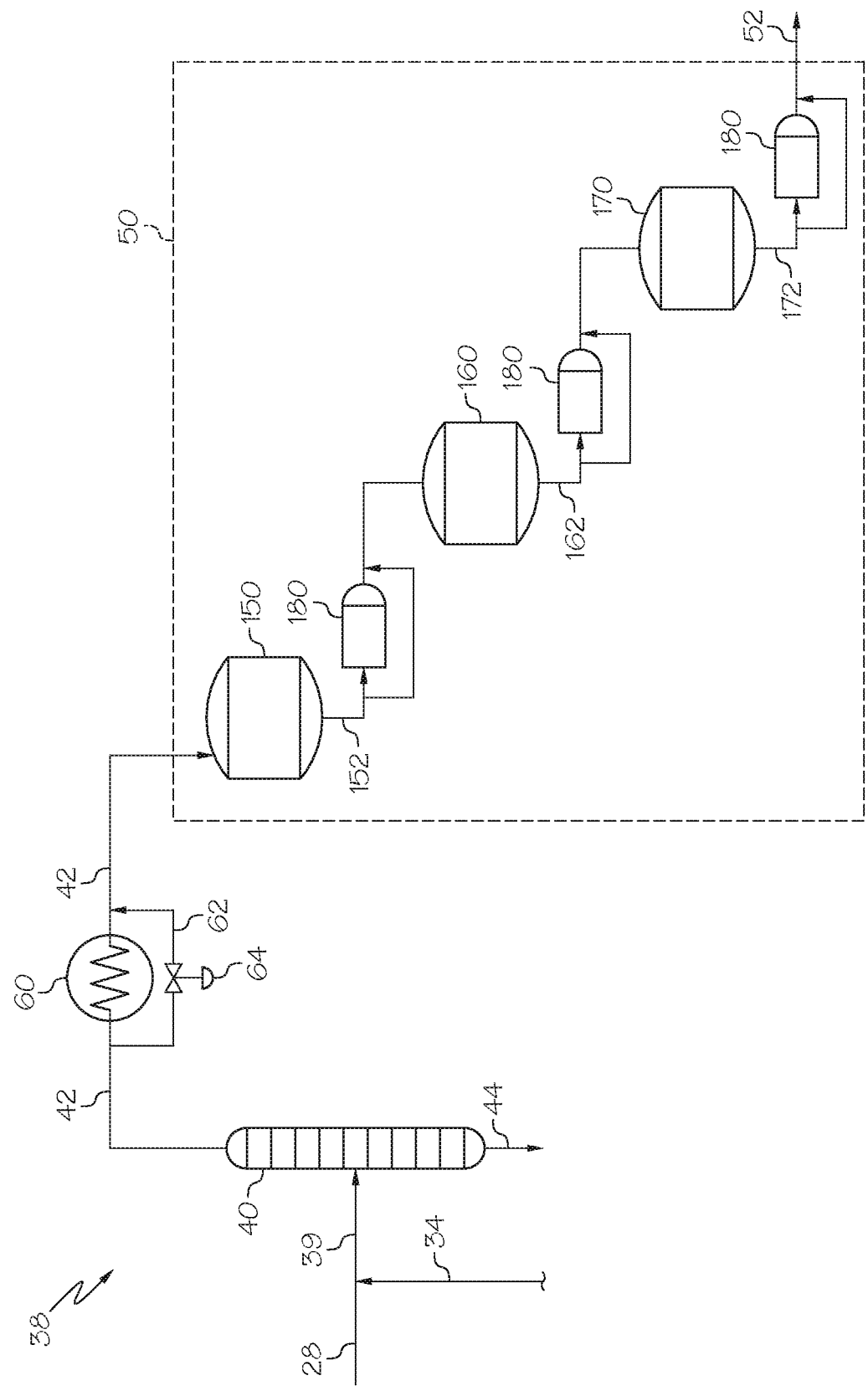
FIG. 4 schematically depicts a portion of the effluent processing system of the integrated process of FIG. 1, according to one or more embodiments shown and described herein.

Referring to FIG. 4, as previously discussed, the effluent processing system 38 may include at least the separation system 40, the acetylene hydrogenation unit 50 downstream of the separation system 40, and the heat exchanger 60 disposed between the separation system 40 and the acetylene hydrogenation unit 50. The cracked gas 28, at least a portion of the FCDh effluent 34, or both may be passed to the separation system 40. In some embodiments, the cracked gas 28 and the FCDh effluent 34 may be independently passed directly to the separation system 40. In some embodiments, the cracked gas 28 and the FCDh effluent 34 may be combined upstream of the separation system 40 and passed as a combined stream 39. The FCDh effluent 34 may be combined with the cracked gas 28 at any point downstream of the water quench unit 130 and oil quench unit 120.

The separation system 40 may be operable to produce at least the hydrogenation feed 42 and an acetylene-depleted stream 44 from the cracked gas 28, the FCDh effluent 34, or both. The separation system 40 may include one or a plurality of separation units. The separation system 40 may include any type of separation units operable to produce the hydrogenation feed 42 from the cracked gas 28, the FCDh effluent 34, or both. In some embodiments, the separation system 40 may include a distillation unit in which the cracked gas 28, the FCDh effluent 34, or both may be separated into the hydrogenation feed 42 and the acetylene-depleted stream 44 by differences in boiling point temperatures of the constituents. In some embodiments, the separation system 40 may be a multiple-stage distillation column. Separation of the constituents of the cracked gas 28, the FCDh effluent 34, or both by difference in boiling point temperature may include initially cooling the cracked gas 28, the FCDh effluent 34, or both to temperatures less than the boiling point temperatures of one or more constituents. Thus, the separation system 40 may include a condenser operable to condense one or more constituents of the cracked gas 28, the FCDh effluent 34, or both upstream of the distillation unit. The separation system 40 is not limited to a distillation process. It is understood that other methods and processes for producing the hydrogenation feed 42 from the cracked gas 28, the FCDh effluent 34, or both are contemplated.

As previously discussed, the hydrogenation feed 42 may include at least 95% by weight of the acetylene from the cracked gas 28 passed to the separation system 40. The hydrogenation feed 42 may include saturated and unsaturated hydrocarbons, such as, but not limited to, ethylene ($C_2H_4$), propylene ($C_3H_6$), acetylene ($C_2H_2$), methyl acetylene ($H_3C$—$C\equiv CH$), propadiene ($H_2C$=$C$=$CH_2$), methane ($CH_4$), ethane ($C_2H_6$), propane ($C_3H_8$), or combinations of these. The hydrogenation feed 42 may also include non-hydrocarbon gases, such as, but not limited to, hydrogen, CO, carbon dioxide ($CO_2$), inert gases, or combinations of these. Inert gases may include nitrogen, argon, or other inert gases present in the steam cracking system 20, the FCDh system 30, or both. In some embodiments, the hydrogenation feed 42 may include acetylene, hydrogen, CO, and at least one product. The hydrogenation feed 42 may further include methyl acetylene, propadiene, or both. The product in the hydrogenation feed 42 may include one or more of ethylene, propylene, methane, ethane, propane, or combinations of these.

The acetylene-depleted stream 44 may include less than 5% by weight of the acetylene from the cracked gas 28. The acetylene-depleted stream 44 may include a greater weight percentage of higher boiling point hydrocarbons compared to the hydrogenation feed 42. These higher boiling point hydrocarbons may include saturated and unsaturated hydrocarbons, such as, but not limited to propane, propylene, butane, butenes, butadiene, pentane, or other higher boiling temperature hydrocarbons.

The separation system 40 may be a front end depropanizer (FEDP) or a front end de-ethanizer (FEDE). When the separation system 40 is an FEDP, the hydrogenation feed 42 may include $C_{3-}$ hydrocarbons and non-hydrocarbon gases. The $C_{3-}$ hydrocarbons may include, but are not limited to, methane, ethane, propane, ethylene, propylene, acetylene, methyl acetylene, propadiene, and combinations of these. The light gases in the hydrogenation feed 42 may include hydrogen, CO, carbon dioxide, nitrogen, or other non-hydrocarbon gases. When the separation system 40 is an FEDP, the acetylene-depleted stream 44 may include the $C_{4+}$ hydrocarbons, such as butane, butenes, butadiene, pentane, pentenes (i.e., one or more of the various isomers of pentene), and other $C_{4+}$ hydrocarbons. In some embodiments, the separation system 40 may be an FEDE, in which case, the greater portions of the propane and propylene may be in the acetylene-depleted stream 44 rather than in the hydrogenation feed 42. In some embodiments, when the separation system 40 is an FEDE, the acetylene-depleted stream 44 may include the greater fraction of methyl acetylene and propadiene compared to the hydrogenation feed 42. Further information on various front end configurations for acetylene hydrogenation in olefin production processes can be found in "Overview on C2 and C3 Selective Hydrogenation in Ethylene Plants" by Edgar L. Mohundro, 15$^{th}$ Ethylene Produces Conference, 2003 AICHE Spring National Meeting, New Orleans, La., the entire contents of which are incorporated herein by reference.

Referring to FIG. 4, the effluent processing system 38 may include the acetylene hydrogenation unit 50 downstream of the separation system 40 and positioned to receive the hydrogenation feed 42 from the separation system 40. The hydrogenation feed 42 may be passed from the separation system 40 to the acetylene hydrogenation unit 50. The hydrogenation feed 42 may be contacted with a hydrogenation catalyst in the acetylene hydrogenation unit 50. The contacting of the hydrogenation feed 42 with the hydrogenation catalyst may cause hydrogenation of at least a portion of the acetylene in the hydrogenation feed 42 to produce the hydrogenated effluent 52, which may have a reduced concentration of acetylene compared to the hydrogenation feed 42. The hydrogenated effluent 52 may include reaction products from the hydrogenation reaction and unreacted constituents of the hydrogenation feed 42. The acetylene hydrogenation unit 50 may include one or a plurality of hydrogenation reactors, such as 1, 2, 3, or more than 3 hydrogenation reactors. The hydrogenation reactors of the acetylene hydrogenation unit 50 may be fixed bed reactors comprising a fixed bed of the hydrogenation catalyst. The hydrogenation reactors of the acetylene hydrogenation unit 50 may be vapor phase reactors operable to conduct the hydrogenation reaction through contact of the hydrogenation catalyst (a solid) with reactants in the vapor phase.

Referring to FIG. 4, in some embodiments, the acetylene hydrogenation unit 50 may include a plurality of hydrogenation reactors arranged in series (e.g., first hydrogenation reactor 150, second hydrogenation reactor 160, and third hydrogenation reactor 170). Referring to FIG. 4, in one embodiment, the acetylene hydrogenation unit 50 may include at least a first hydrogenation reactor 150 and a second hydrogenation reactor 160 downstream of the first hydrogenation reactor 150. The acetylene hydrogenation unit 50 may also include a third hydrogenation reactor 170 downstream of the second hydrogenation reactor 160. The first hydrogenation reactor 150 may remove a majority of the acetylene in the hydrogenation feed 42, while the second reactor 160 may remove the rest of acetylene. The third reactor 170 may function as a polishing bed to prevent the hydrogenated effluent 52 from being out-of-specification for acetylene concentration. The acetylene hydrogenation unit 50 may also optionally include heat exchangers 180 disposed between each of the hydrogenation reactors. The heat exchangers 180 may be operable to remove heat generated from the exothermic hydrogenation reaction between the hydrogenation reactors.

The hydrogenation feed 42 may be passed to the first hydrogenation reactor 150, which may be operable to hydrogenate at least acetylene from the hydrogenation feed 42 to produce a first hydrogenated effluent 152. The first hydrogenated effluent 152 may have a concentration of acetylene less than the concentration of acetylene in the hydrogenation feed 42. The first hydrogenation reactor 150 may have an acetylene conversion of greater than or equal to 85%, greater than or equal to 90%, or greater than or equal to 95% during normal operating conditions of the acetylene hydrogenation unit 50 in order to maintain the concentration of acetylene in the hydrogenated effluent 52 less than the threshold acetylene concentration. Heat may be removed from the first hydrogenated effluent 152 by passing the first hydrogenated effluent 152 through a heat exchanger 180. The first hydrogenated effluent 152 may be passed on the to the second hydrogenation reactor 160, which may be operable to further hydrogenate acetylene in the first hydrogenated effluent 152 to produce a second hydrogenated effluent 162. Heat may be removed from the second hydrogenated effluent 162 by passing the second hydrogenated effluent 162 through a heat exchanger 180. The second hydrogenated effluent 162 may be passed on the to the third hydrogenation reactor 170, which may be operable to further hydrogenate acetylene in the second hydrogenated effluent 162 to produce a third hydrogenated effluent 172. Heat may be removed from the third hydrogenated effluent 172 by passing the third hydrogenated effluent 172 through a heat exchanger 180. The third hydrogenated effluent 172 may be passed out of the acetylene hydrogenation unit 50 as the hydrogenated effluent 52.

Although not depicted in the figures, the acetylene hydrogenation unit 50 may include one or a plurality of temperature sensors, pressure sensors, flow meters, or combinations of these for measuring the temperature, pressure, or gas flow rates at one or a plurality of positions of the acetylene hydrogenation unit 50. The temperature, pressure, and/or gas flow rate may be determined for one or more of the plurality of acetylene hydrogenation reactors of the acetylene hydrogenation unit 50 and/or for the hydrogenation feed 42 introduced to the acetylene hydrogenation unit 50. The method of operating the acetylene hydrogenation unit 50 may include determining the temperature of the acetylene hydrogenation unit 50, the temperature of the hydrogenation feed 42 passed to the acetylene hydrogenation unit 50, or both.

The acetylene hydrogenation unit 50 may also include one or a plurality of analyzers, such as GC analyzers, operable to measure the concentration of CO, hydrogen, or other constituents in the hydrogenation feed 42, the hydrogenated effluent 52, intermediate effluents from one or more of the hydrogenation reactors of the acetylene hydrogenation unit 50, or combinations of these. In some embodiments, the stream for composition analysis may be retrieved from the hydrogenation feed 42 before introducing the hydrogenation feed 42 to the acetylene hydrogenation unit 50. Alternatively or additionally, the stream for composition analysis may be retrieved from the hydrogenated effluent 52 passed out of the acetylene hydrogenation unit 50. In some embodiments, the stream for composition analysis may be retrieved from one or more intermediate effluent streams passed of one of the hydrogenation reactors of the acetylene hydrogenation unit 50. The method of operating the acetylene hydrogenation unit 50 may include determining the concentration of CO, hydrogen, or other constituent in the acetylene hydrogenation unit 50.

The hydrogenation catalyst may be an acetylene hydrogenation catalyst that is a catalyst selective for hydrogenating acetylene relative to product compounds in the hydrogenation feed 42. The hydrogenation catalyst may be any known catalyst for selectively hydrogenating acetylene. Commercial catalysts for acetylene hydrogenation are widely available, and the present disclosure is not limited to any specific composition recited herein.

The acetylene hydrogenation unit 50 can be operated at conditions under which the catalytic hydrogenation is selective for hydrogenation of acetylene over hydrogenation of propylene and ethylene. The acetylene hydrogenation unit 50 may be operated at a temperature sufficient to hydrogenate acetylene at a conversion rate that prevents breakthrough of acetylene to downstream processes, but less than a temperature resulting in increased hydrogenation of olefins and thermal runaway of the acetylene hydrogenation unit 50. The operating temperature of the acetylene hydrogenation unit 50 may be from 10° C. to 200° C., such as from 10° C. to 100° C., although the operating temperature of the acetylene hydrogenation unit 50 may depend on the composition of the hydrogenation feed 42, as will be discussed in further detail herein. Other factors influencing the operating temperature of the acetylene hydrogenation unit 50 may include, but are not limited to, the type of hydrogenation catalyst, the age/activity of the hydrogenation catalyst, flow rate, inlet acetylene concentration, CO concentration, presence of contaminants or poisons, other factors, or combinations of these. The acetylene hydrogenation unit 50 may operate at a pressure of from 100 pounds per square inch gauge (psig) to 1000 psig (i.e., about 690 kilopascals (kPa) to about 6900 kPa). The acetylene hydrogenation unit 50 may additionally operate at a gas hourly space velocity (GHSV) of from 1,000 to 14,000 (volume per volume of catalyst per hour).

When operating under normal operation conditions, a conversion of acetylene in the first hydrogenation reactor 150 of the acetylene hydrogenation unit 50 may be sufficient to maintain a concentration of acetylene in the hydrogenated effluent 52 less than or equal to the threshold acetylene concentration. In some embodiments, the acetylene conversion in the first hydrogenation reactor 150 may be greater than or equal to 85% under normal operation conditions, such as greater than or equal to 88%, greater than or equal to 90%, or even greater than or equal to 95%. Normal operation conditions refer to operation of the acetylene hydrogenation unit 50 at steady state with the acetylene concentration in the hydrogenated effluent 52 less than or equal to the threshold acetylene concentration. In some embodiments, under normal operation conditions, the acetylene conversion in the first hydrogenation reactor 150 may be from 85% to 95%, or from 88% to 92%.

The hydrogenated effluent 52 may refer to the effluents or compositions passed out of the acetylene hydrogenation unit 50, such as out of the last hydrogenation reactor of the acetylene hydrogenation unit 50. The hydrogenated effluent 52 may have an acetylene concentration less than the acetylene concentration of the hydrogenation feed 42. The hydrogenated effluent 52 may have an acetylene concentration of less than or equal to a threshold acetylene concentration, which may be specified by the olefin product user. In some embodiments, the hydrogenated effluent 52 may have an acetylene concentration of less than or equal to 2 part per million by volume (ppmv), less than or equal to 1 ppmv, less than or equal to 0.5 ppmv, or even less than or equal to 0.1 ppmv. The hydrogenation reaction in the acetylene hydrogenation unit 50 may consume hydrogen from the hydrogenation feed 42, but the change in concentration of hydrogen in the hydrogenated effluent 52 compared to the hydrogenation feed 42 may be less than the measurement uncertainty of analytical instruments due to the small concentrations of acetylene relative to the concentration of hydrogen in the hydrogenation feed 42. The hydrogenation catalyst and operating conditions of the acetylene hydrogenation unit 50 may be selective for hydrogenating acetylene relative to hydrogenation of product compounds, such as propylene and ethylene, produced in the steam cracking system 20 and/or the FCDh system 30.

Referring again to FIG. 4, the effluent processing system 38 may include a heat exchanger 60 disposed between the separation system 40 and the acetylene hydrogenation unit 50. The heat exchanger 60 may include the bypass 62 having a control valve 64. The temperature of the hydrogenation feed 42 at the inlet of the acetylene hydrogenation unit 50 may be increased or decreased by controlling the amount of the hydrogenation feed 42 passing through the heat exchanger 60 and the amount of the hydrogenation feed 42 bypassing the heat exchanger 60 through the bypass 62. Controlling an amount of the hydrogenation feed 42 bypassed around the heat exchanger 60 may allow for increasing or decreasing the temperature of the hydrogenation feed 42 at the inlet of the acetylene hydrogenation unit 50. The heat exchanger 60 for the hydrogenation feed 42 may be any type of heat exchanger known in the chemical industry.

In some embodiments, the effluent processing system 38 may include an acid gas removal process (not shown) downstream of the separation system 40. The acid gas removal process may be operable to remove acid gases from the hydrogenation feed 42, such as through scrubbing, upstream of the acetylene hydrogenation unit 50. In some embodiments, the acid gas removal process may be disposed between the separation system 40 and the heat exchanger 60. As previously discussed, in some embodiments, the acid gas removal process may be disposed upstream of the separation system 40.

The hydrogenated effluent 52 may be passed to one or more unit operations and/or processes downstream of the acetylene hydrogenation unit 50 for further processing of the hydrogenated effluent 52. Downstream processes may include vapor compression, separation, drying, or other operations and processes. The unit operations and processes downstream of the acetylene hydrogenation unit 50 may, ultimately, separate the hydrogenated effluent 52 into a plurality of gaseous streams, such as, but not limited to, an ethylene product stream, a propylene product stream, a propane stream, other streams, or combinations of these streams. One or more of these product streams may be passed as reactants or raw materials to further production processes, such as polymer production processes.

Figure 5:
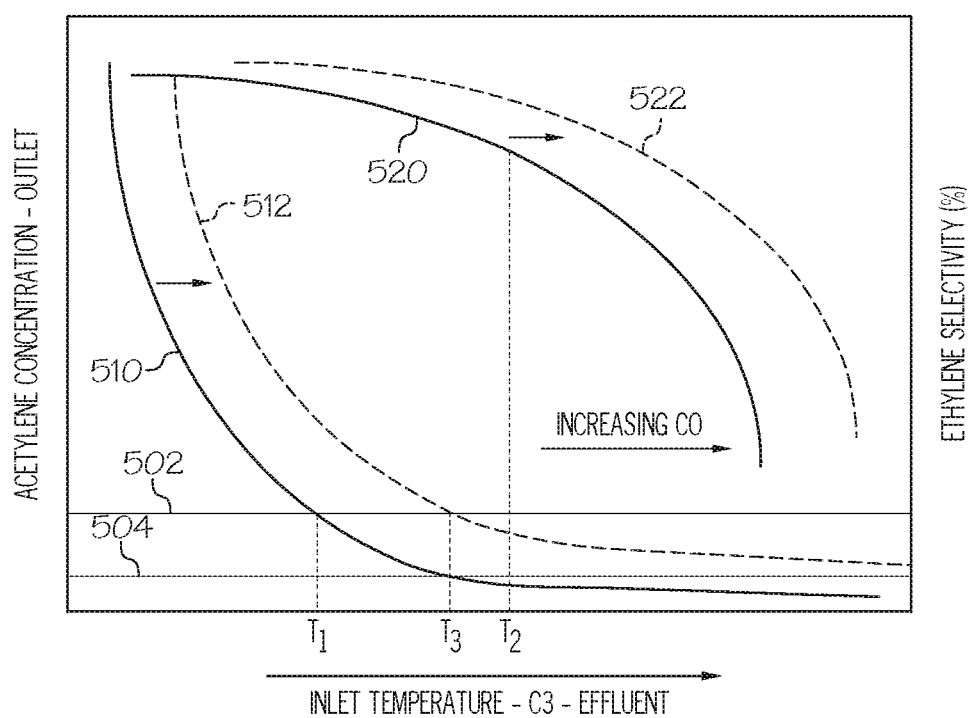
FIG. 5 graphically depicts a concentration of acetylene (y-axis-left) and an ethylene selectivity (y-axis-right) for an acetylene hydrogenation unit as a function of a temperature (x-axis) of a hydrogenation feed passed to the acetylene hydrogenation unit, according to one or more embodiments shown and described herein.

Referring now to FIG. 5, the acetylene concentration in the hydrogenated effluent 52 (y-axis left) and the ethylene selectivity of the acetylene hydrogenation unit 50 (y-axis right) are depicted as functions of the temperature (x-axis) of the hydrogenation feed 42 at the inlet to the acetylene hydrogenation unit 50. Line 502 in FIG. 5 represents a threshold acetylene concentration for the hydrogenated effluent 52, below which the concentration the acetylene may be considered reduced to a level sufficient to satisfy the requirements of olefin users and/or to prevent or reduce fouling of catalysts, out-of-specification product streams, or other issues in downstream processes. As shown in FIG. 5, the acetylene concentration (curve 510) in the hydrogenated effluent 52 decreases with increasing inlet temperature for a given composition of the hydrogenation feed 42. FIG. 5 shows that the acetylene concentration 510 in the hydrogenated effluent 52 can be increased or decreased by decreasing or increasing, respectively, the inlet temperature to the acetylene hydrogenation unit 50. Temperature $T_1$ for the given composition of the hydrogenation feed 42 for curve 510 can be defined as the lowest temperature at which the acetylene concentration in the hydrogenated effluent 52 is equal to or less than the threshold acetylene concentration 502. At temperatures of the hydrogenation feed 42 greater than $T_1$ the acetylene concentration (510) in the hydrogenated effluent 52 is less than the threshold acetylene concentration. For temperatures of the hydrogenation feed 42 less than $T_1$, the acetylene concentration (510) in the hydrogenated effluent 52 may be greater than the threshold acetylene concentration.

FIG. 5 also shows the ethylene selectivity of the acetylene hydrogenation unit 50 (curve 520) as a function of inlet temperature for the same composition of the hydrogenation feed 42 as curve 510. As shown in FIG. 5, the ethylene selectivity (curve 520) decreases with increasing inlet temperature. Thus, as the inlet temperature to the acetylene hydrogenation unit 50 increases, the ethylene selectivity of the acetylene hydrogenation unit 50 decreases, indicating that more acetylene and/or even some ethylene is converted to ethane, which may be caused by increased hydrogenation of ethylene in the acetylene hydrogenation unit 50. Increased hydrogenation of ethylene may lead to thermal runaway. For example, at temperatures of the hydrogenation feed 42 greater than temperature $T_2$, the ethylene selectivity may decrease to a point at which an unacceptable amount of ethylene undergoes hydrogenation. Since the ethylene hydrogenation reaction is exothermic, additional heat from the increased hydrogenation of ethylene and other olefins is released and may further increase the temperature in the acetylene hydrogenation unit 50, which further shifts the hydrogenation reaction towards hydrogenation of ethylene and propylene. The increasing heat generated from increasing hydrogenation of ethylene and other olefins may lead to thermal runaway of the acetylene hydrogenation unit 50. Thermal runaway can result in increased loss of olefin products through over-hydrogenation of the ethylene and propylene. Additionally, the increased temperatures in excess of 200° C. experienced during thermal runaway can damage the hydrogenation catalyst and equipment, such as reactors, instruments, heat exchangers, and other equipment, and may increase safety risks.

Referring again to FIG. 5, an operating window for the inlet temperature of the hydrogenation feed 42 introduced to the acetylene hydrogenation unit 50 for a given composition of the hydrogenation feed 42 can be defined between the inlet temperature $T_1$, below which the acetylene concentration in the hydrogenated effluent 52 is greater than the threshold acetylene concentration 502, and the inlet temperature $T_2$, above which the ethylene selectivity decreases and hydrogenation of olefin products can result in thermal runaway of the acetylene hydrogenation unit 50.

Changes in the CO concentration of the hydrogenation feed 42 may change the operating window of the acetylene hydrogenation unit 50. Increasing the CO concentration in the hydrogenation feed 42 may shift the process window for the temperature of the hydrogenation feed 42 towards greater temperatures and widen the process window. In FIG. 5, curve 512 may represent the acetylene concentration in the hydrogenated effluent 52 as a function of inlet temperature of the hydrogenation feed 42 for operation of the acetylene hydrogenation unit 50 with a greater concentration of CO, such as when the FCDh effluent is integrated into the effluent processing system 38, compared to the concentration of CO for curve 510 (e.g., when only the cracked gas 28 is passed to the effluent processing system 38). At a given temperature of the hydrogenation feed 42, increasing the concentration of CO reduces the conversion of acetylene. By increasing the concentration of CO in the acetylene hydrogenation unit 50, the inlet temperature $T_3$ of the hydrogenation feed 42 at which the acetylene concentration in the hydrogenated effluent 52 is equal to the threshold acetylene concentration 502 is greater than the corresponding temperature $T_1$ of the hydrogenation feed 42 for curve 510 (having a lesser concentration of CO).

Increasing the CO concentration in the acetylene hydrogenation unit 50 may also shift the ethylene selectivity curve toward a higher inlet temperature. Referring to FIG. 5, ethylene selectivity curve 522 represents the ethylene selectivity for the acetylene hydrogenation unit 50 as a function of inlet temperature of hydrogenation feed for a greater CO concentration (e.g., such as when the FCDh effluent 34 is integrated into the effluent processing system 38) compared to the CO concentration for curve 520 (e.g., when only the cracked gas 28 is passed to the effluent processing system 38). As shown in FIG. 5, increasing the CO concentration (curve 522) in the acetylene hydrogenation unit 50 can increase the ethylene selectivity at a given temperature. This may enable operation of the acetylene hydrogenation unit 50 at greater inlet temperatures compared to operating the acetylene hydrogenation unit 50 with a lesser concentration of CO. However, a sudden decrease in the concentration of CO in the hydrogenation feed due to decrease or complete loss of flow of the FCDh effluent 34 may greatly increase the catalyst activity in the hydrogenation unit at the same temperature and may shift the process to lower olefin selectivity, resulting in increased hydrogenation of olefin products, such as ethylene and/or propylene, which can lead to thermal runaway as previously discussed herein.

Referring again to FIG. 1, the steam cracking system 20 and the FCDh system 30 may be integrated so that these processes share a common effluent processing system 38, which may include at least the separation system 40 and acetylene hydrogenation unit 50. The steam cracking system 20 can be operated, and the cracked gas 28 may be passed to the effluent processing system 38. The FCDh system 30 may also be operated, and at least a portion of the FCDh effluent 34 from the FCDh system 30 may be integrated into the effluent processing system 38. The portion of the FCDh effluent 34 may be integrated into the effluent processing system 38 by passing the portion of the FCDh effluent 34 to the separation system 40, combining the portion of the FCDh effluent 34 with the cracked gas 28 upstream of the separation system 40, or both. In some embodiments, the entire FCDh effluent 34 may be passed to the separation system 40, combined with the cracked gas 28, or both. In some embodiments, only a portion of the FCDh effluent 34 may be passed to the separation system 40, combined with the cracked gas 28, or both. The remaining FCDh effluent may be recycled back to the FCDh system 30 or back into combination with the second hydrocarbon feed 32 via FCDh effluent recycle 36. Additionally, in some embodiments, the portion of the FCDh effluent 34 passed to the separation system 40, combined with the cracked gas 28, or both, may be a second portion of the FCDh effluent supplementing a first portion of the FCDh effluent already being passed into the effluent processing system 38.

As previously discussed, the concentration of CO in the FCDh effluent 34 may be greater than the concentration of CO in the cracked gas 28. The cracked gas 28 may have a concentration of CO of from 50 ppmv to 400 ppmv. The FCDh effluent 34 may have a concentration of CO of from 600 ppmv to 2400 ppmv, such as from 1000 ppmv to 2000 ppmv. When both the cracked gas 28 and the portion of the FCDh effluent 34 are passed to the effluent processing system 38, the amount of CO in the hydrogenation feed 42 may be greater than the amount of CO in the cracked gas 28.

Unit trip of the FCDh system 30 may cause a complete shutdown or the FCDh system 30 or recycle of a greater portion of the FCDh effluent 34 back to the FCDh system 30 through FCDh recycle 36. When this happens, the flow of the FCDh effluent 34 to the effluent processing system 38 may be suddenly decreased (e.g., through increased recycle back to the FCDh system 30) or eliminated (e.g., complete shutdown of the FCDh system 30 and reduction of the flowrate of the FCDh effluent 34 to zero, or complete disconnection of the FCDh system 30 from the effluent processing system 38. A substantial reduction in or complete loss of flow of the portion of the FCDh effluent 34 to the separation system 40 (e.g., directly or in combination with the cracked gas 28) may result in a decrease in the concentration of CO in the hydrogenation feed 42 to the acetylene hydrogenation unit 50.

As previously discussed, decreasing the concentration of CO in the hydrogenation feed 42, which decreases the CO concentration in the acetylene hydrogenation unit 50, may increase hydrogenation of ethylene and other olefin products in the acetylene hydrogenation unit 50, thereby decreasing the ethylene selectivity. The decreased concentration of CO in the hydrogenation feed 42 due to decrease or complete loss of flow of the FCDh effluent 34 to the effluent processing system 38 may increase activity of the hydrogenation catalyst and increase the reaction rate, at constant temperature, of the hydrogenation reaction of acetylene. The increased reaction rate may increase the hydrogenation of ethylene and other product olefins and reduce the ethylene selectivity. A reduction in or complete loss of flow of the FCDh effluent 34 may also decrease the mass flow rate of the hydrogenation feed 42 and mass flow rate through the acetylene hydrogenation unit 50. This could lead to smaller gas hourly space velocity or residence time of the hydrogenation feed, which may increase the hydrogenation of ethylene and other product olefins in the acetylene hydrogenation unit 50. As previously discussed, the increased hydrogenation of ethylene and other olefins in the acetylene hydrogenation unit 50 may lead to thermal runaway of the acetylene hydrogenation unit. Thermal runaway can result in increased loss of olefin products through over-hydrogenation of the ethylene and propylene. Additionally, the increased temperatures in excess of 200° C. experienced during thermal runaway can damage the hydrogenation catalyst and equipment, such as reactors, instruments, heat exchangers, and other equipment, and may increase safety risks. Thermal runaway may also result in unit trip or shutdown of the steam cracking system 20.

Referring again to FIG. 1, the methods disclosed herein for operating the acetylene hydrogenation unit 50 may include operating the acetylene hydrogenation unit 50 with an increased amount of CO contributed by the cracked gas 28 relative to the amount of CO contributed by the FCDh effluent 34. As used herein, the term "cracker CO" may refer to the portion of the CO in the hydrogenation feed 42 contributed by the cracked gas 28, and the term "FCDh CO" may refer to the portion of the CO in the hydrogenation feed 42 contributed by the FCDh effluent 34. The methods for operating the acetylene hydrogenation unit 50 may include operating the acetylene hydrogenation unit 50 under conditions in which at least 20% of the total CO in the hydrogenation feed is from the cracked gas 28. The total CO in the hydrogenation feed 42 may be the sum of the cracker CO from the cracked gas 28 and the FCDh CO from the FCDh effluent 34. The methods for operating the acetylene hydrogenation unit 50 may also include operating the steam cracking system 20 under conditions that increase the CO production such that a concentration of CO in the cracked gas 28 is great enough that when a flowrate of the FCDh effluent 34 is zero, a CO concentration in the hydrogenation feed 42 is at least 100 ppmv.

Operating the acetylene hydrogenation unit 50 with at an increased proportion of cracker CO contributed by the cracked gas 28 relative to the FCDh CO contributed by the FCDh effluent 34, may reduce the effects of a sudden reduction in or complete loss of flow of the FCDh effluent 34 to the effluent processing system 38. This may reduce or prevent thermal runaway of the acetylene hydrogenation unit 50 in response to a unit trip or shutdown of the FCDh system 30 resulting in a reduction in or loss of flow of the FCDh effluent 34 to the effluent processing system 38.

Referring again to FIGS. 1 and 2, the proportion of cracker CO in the hydrogenation feed 42 may be increased by increasing the amount of CO in the cracked gas 28. The amount of CO in the cracked gas 28 may be increased by operating the steam cracking system 20 under conditions that increase the amount of CO produced in the steam cracking system 20. Operating the steam cracking system 20 under conditions that increase the amount of CO in the cracked gas 28 may include changing one or more operating parameters of the steam cracking unit 110 (FIG. 2) of the steam cracking system 20. In some embodiments, operating the steam cracking system 20 under conditions that increase the CO concentration in the cracked gas 28 may include changing the amount of sulfur-containing compounds, methanol, or both, introduced to the steam cracking unit 110. In some embodiments, the concentration of CO in the cracked gas 28 can be increased or decreased by decreasing or increasing, respectively, the amount of sulfur-containing compounds introduced to the steam cracking unit 110. Sulfur-containing compounds may include, but are not limited to, one or more of dimethyl disulfide (DMDS), dimethyl sulfide (DMS), diethyl disulfide (DEDS), methyl mercaptan (MM), or combination thereof. The amount of sulfur-containing compounds introduced to the steam cracking unit 110 may be increased or decreased by increasing or decreasing the flow rate of sulfur-containing compounds 24 passed to the steam cracking unit 110 and/or combined with the first hydrocarbon feed 22 upstream of the steam cracking unit 20. Not intending to be limited by any particular theory, it is believed that increasing the sulfur-containing compounds 24 introduced to the steam cracking unit 110 may passivate the heating elements in the cracking furnace of the steam cracking unit 20, thereby controlling the amount of coke formed in the steam cracking unit 110 and the amount of CO produced.

Although normally added to the steam cracking unit 110 as an anti-freezing agent, the amount of methanol introduced to the steam cracking unit 110 may also influence the amount of CO produced in the steam cracking system 20. The amount of methanol passed to the steam cracking unit 110 may be increased or decreased by increasing or decreasing the flow rate of the methanol-containing stream 26 passed to the steam cracking unit 110.

Increasing the amount of the cracker CO in the hydrogenation feed 42 may increase the total amount of CO in the hydrogenation feed 42. Increasing the total amount of CO in the hydrogenation feed 42 may be accompanied by an increase in the temperature of the hydrogenation feed 42 to position the operating conditions of the acetylene hydrogenation unit 50 within the process window corresponding to the increased CO concentration. Increasing the temperature of the hydrogenation feed 42 according to the increased concentration of CO in the hydrogenation feed 42 may increase the conversion of acetylene in the acetylene hydrogenation unit 50 so that the concentration of acetylene in the hydrogenated effluent 52 is less than the threshold acetylene concentration. The temperature of the hydrogenation feed 42 may be sufficient to maintain the acetylene concentration of the hydrogenated effluent 52 passed out of the acetylene hydrogenation unit 50 less than the threshold acetylene concentration, such as less than or equal to 2 ppm by volume (ppmv), less than or equal to 1 ppmv, less than or equal to 0.5 ppmv, or even less than or equal to 0.1 ppmv. As previously discussed, the temperature of the hydrogenation feed 42 may be controlled by controlling an amount of the hydrogenation feed 42 bypassed around the heat exchanger 60 through bypass 64. Other methods of the controlling the temperature of the hydrogenation feed 42 and/or the acetylene hydrogenation unit 50 are also contemplated.

Referring again to FIG. 1, in the integrated process 10 for producing olefins, the steam cracking system 20 may have a capacity greater than the capacity of the FCDh system 30 so that the flow rate of the portion of the cracked gas 28 in the hydrogenation feed 42 is greater than a flow rate of the portion of the FCDh effluent 34 passed to the effluent processing system 38 (e.g., combined with the cracked gas 28, passed to the separation system 40, or both). The relative size of the FCDh system 30 to the steam cracking system 20 in the integrated system 10 may be characterized by a flow ratio. As used herein, the "flow ratio" of the integrated process 10 may be a ratio of the mass flow rate of the portion of the FCDh effluent 34 from the FCDh system 30 passed to the separation system 40 divided by a mass flow rate of a portion of the hydrogenation feed 42 contributed by the cracked gas 28. The portion of the hydrogenation feed 42 contributed by the cracked gas 28 refers to the portions of the cracked gas 28 that are separated into the hydrogenation feed 42 by the separation system 40 and does not include those portions of the cracked gas 28 that end up in the acetylene-depleted stream 44. For an FEDP configuration, the portion of the hydrogenation feed 42 contributed by the cracked gas 28 may include at least 95% of the C3 and C3– constituents, CO, and hydrogen from the cracked gas 28. For an FEDE configuration, the portion of the hydrogenation feed 42 contributed by the cracked gas may include at least 95% of the C2 and C2– constituents, CO, and hydrogen from the cracked gas 28. The flow ratio for the integrated process 10 for producing olefins may be less than or equal to 1/2, less than or equal to 1/4, less than or equal to 1/8, or less than or equal to 1/12.

Alternatively, the relative size of the FCDh system 30 to the steam cracking system 20 in the integrated system 10 may be characterized by a size ratio, which may be defined as a ratio of the mass flow rate of the portion of the FCDh effluent 34 from the FCDh system passed to the separation system 40 divided by a mass flow rate of the cracked gas 28 passed to the separation system 40. The size ratio may generally be less than the flow ratio. In some embodiments, the integrated process 10 for producing olefins may have a size ratio of the FCDh system 30 to the steam cracking system 20 of less than 1/2, less than 1/4, less than 1/8, or even less than 1/12.

In some embodiments, the steam cracking system 20 may be operated under conditions that increase CO production such that a concentration of CO in the cracked gas 28 is great enough that when a flowrate of the FCDh effluent 34 is zero, the CO concentration in the hydrogenation feed 42 is at least 100 ppmv. In other words, the steam cracking system 20 may be operated under conditions in which the amount of CO in the cracked gas 28 is sufficient to produce a CO concentration in the hydrogenation feed 42 of at least 100 ppmv when the flow rate of the FCDh effluent 34 is discontinued. Operating the steam cracking system 20 under conditions that maintain an increased amount of CO in the cracked gas 28 sufficient to produce a CO concentration in the hydrogenation feed 42 of greater than 110 ppmv when the flowrate of the FCDh effluent 34 is zero may reduce or prevent thermal runaway of the acetylene hydrogenation unit 50 in response to a disruption in the flow of the FCDh effluent 34 to the acetylene hydrogenation unit 50. In some embodiments, the steam cracking system 20 may be operated under conditions that increase CO production such that a concentration of CO in the cracked gas 28 is great enough that when a flowrate of the FCDh effluent 34 is zero, the CO concentration in the hydrogenation feed 42 may be greater than or equal to 150 ppmv, or even greater than or equal to 200 ppmv based on the volume of the hydrogenation feed 42. In some embodiments, the steam cracking system 20 may be operated under conditions that increase CO production such that a concentration of CO in the cracked gas 28 is great enough that when a flowrate of the FCDh effluent 34 is zero, the CO concentration in the hydrogenation feed 42 may be from 100 ppmv to 450 ppmv, from 100 ppmv to 200 ppmv, from 150 ppmv to 400 ppmv, or from 200 ppmv to 450 ppmv based on the total volume of the hydrogenation feed 42.

In some embodiments, the amount of the cracker CO in the hydrogenation feed 42 may be greater than or equal to 20% of the total amount of CO in the hydrogenation feed 42. The total amount of CO in the hydrogenation feed 42 may include both the cracker CO contributed by the cracked gas 28 and the FCDh CO contributed by the FCDh effluent 34. Maintaining the amount of cracker CO in the hydrogenation feed 42 greater than or equal to 20% of the total amount of CO in the hydrogenation feed 42 may be in addition to or as an alternative to operating the steam cracking system 20 under conditions that increase CO production such that a concentration of CO in the cracked gas 28 is great enough that when a flowrate of the FCDh effluent 34 is zero, the CO concentration in the hydrogenation feed 42 is greater than or equal to 100 ppmv. Operating the acetylene hydrogenation unit 50 with the amount of the cracker CO in the hydrogenation feed 42 greater than or equal to 20% of the total CO in the hydrogenation feed 42 may reduce or prevent thermal runaway of the acetylene hydrogenation unit 50 in response to a disruption in flow of the FCDh effluent 34 to the acetylene hydrogenation unit 50. In some embodiments, the acetylene hydrogenation unit 50 may be operated with an amount of cracker CO of from 20% to 90% of the total amount of CO in the hydrogenation feed 42. In some embodiments, the amount of FCDh CO in the hydrogenation feed 42 may be less than 80% of the total amount of CO in the hydrogenation feed 42. In other words, the amount of CO contributed by the FCDh effluent 34 (i.e., FCDh CO) in the hydrogenation feed 42 may be less than 80% of the total amount of CO in the hydrogenation feed 42, where the total amount of CO in the hydrogenation feed 42 includes at least the FCDh CO and the cracker CO. The amount of the cracker CO in the hydrogenation feed 42 may be greater than or equal to 20% by mass of the total amount of CO in the hydrogenation feed 42.

Referring to FIG. 4, in some embodiments, the amount of cracker CO in the hydrogenation feed 42 may be sufficient to limit a change in a Delta T of the first hydrogenation reactor 150 to less than or equal to 10° C., less than or equal to 8° C., or even less than or equal to 4° C. in response to a decrease or loss of flow of the FCDh effluent 34. The Delta T of the first hydrogenation reactor 150 may refer to an absolute value of a difference between an outlet temperature, which may be a temperature of the first hydrogenated effluent 152 at the outlet of the first hydrogenation unit 150, and an inlet temperature, which may be a temperature of the hydrogenation feed 42 at the inlet to the first hydrogenation unit 150. An increase in the Delta T for the first hydrogenation reactor 150 of greater than 10° C. in response to a decrease or loss of flow of the FCDh effluent 34 (i.e., sudden decrease in CO concentration of hydrogenation feed 42) may increase the probability of thermal runaway of the acetylene hydrogenation unit 50. Thus, maintaining the Delta T of the first hydrogenation reactor 150 less than 10° C. in response to a sudden decrease in CO concentration may, therefore, reduce the probability of thermal runaway of the acetylene hydrogenation unit 50. Maintaining the change in Delta T of the first hydrogenation reactor 150 less than 10° C. in response to a decrease or loss of flow of the FCDh effluent 34 may be accomplished by operating the acetylene hydrogenation unit 50 with an increased amount of cracker CO in the hydrogenation feed 42 contributed by the cracked gas 28.

Referring again to FIG. 4, in some embodiments, the amount of cracker CO in the hydrogenation feed 42 may be sufficient to maintain a change in overall ethylene selectivity in the acetylene hydrogenation unit 50 (including reactor 150, reactor 160, and optionally a third reactor 170) of less than or equal to 80% in response to a decrease or loss of flow of the FCDh effluent 34. Maintaining the loss in overall ethylene selectivity in the acetylene hydrogenation unit 50 less than or equal to 80% in response to a decrease or loss of flow of the FCDh effluent 34 may reduce the probability of thermal runaway of the acetylene hydrogenation unit 50. A loss in ethylene selectivity in the acetylene hydrogenation unit 50 of less than or equal to 80% in response to a decrease or loss of flow of the FCDh effluent 34 into the integrated system 10 may be accomplished by operating the acetylene hydrogenation unit 50 with an increased amount of cracker CO in the hydrogenation feed 42 contributed by the cracked gas 28.

Referring again to FIG. 1, in some embodiments, the acetylene hydrogenation unit 50 may be operated with an amount of FCDh CO in the hydrogenation feed 42 of less than 80% of the total amount of CO in the hydrogenation feed 42, and the method may include combining a supplemental CO stream (not shown) with the hydrogenation feed 42, or the cracked gas 28, or both upstream of the acetylene hydrogenation unit 50. In these embodiments, the total amount of CO in the hydrogenation feed 42 may include the FCDh CO, the cracker CO, and the supplemental CO. Thus, the amount of the FCDh CO in the hydrogenation feed 42 may be maintained at less than 80% of the total amount of CO in the hydrogenation feed 42 by introducing the supplemental CO to increase the total amount of CO in the hydrogenation feed 42. Introducing a supplemental CO stream may be in addition to or as an alternative to increasing the amount of CO produced in the steam cracking unit 110, as previously discussed.

Referring again to FIG. 1, a method for operating the acetylene hydrogenation unit 50 in an integrated steam cracking-fluidized catalytic dehydrogenation (FCDh) system 10 may include cracking at least a portion of the first hydrocarbon feed 22 in the steam cracking system 20 to produce the cracked gas 28 comprising at least hydrogen, carbon monoxide (CO), and acetylene and dehydrogenating at least a portion of the second hydrocarbon feed 32 in the FCDh system 30 to produce the FCDh effluent 34 comprising at least hydrogen and CO. The first hydrocarbon feed 22, the second hydrocarbon feed 32, the cracked gas 28, and the FCDh effluent 34 may each have any of the compositions, properties, and/or characteristics previously described herein for the first hydrocarbon feed 22, second hydrocarbon feed 32, cracked gas 28, and FCDh effluent 34, respectively. The method may further include separating the cracked gas 28 and at least a portion of the FCDh effluent 34 into the hydrogenation feed 42 and the acetylene-depleted stream 44. The hydrogenation feed 42 may include at least hydrogen, CO, and acetylene. The hydrogenation feed 42 may include at least 99% of the CO from the cracked gas 28 and the FCDh effluent 34. During normal operating conditions, at least 20% of the CO in the hydrogenation feed 42 may be from the cracked gas 28. The method may further include contacting the hydrogenation feed 42 with the acetylene hydrogenation catalyst in the acetylene hydrogenation unit 50, the contacting causing hydrogenation of at least a portion of the acetylene in the hydrogenation feed 42 to produce the hydrogenated effluent 52. The steam cracking system 20 may be operated under conditions that increase CO production such that a concentration of CO in the cracked gas 28 is great enough that when a flowrate of the FCDh effluent 34 is zero, a CO concentration in the hydrogenation feed 42 is at least 100 ppmv. The steam cracking system 20, the FCDh system 30, the separation system 40, and the acetylene hydrogenation unit 50 may have any of the features or characteristics described herein for each of these respective systems and units. The integrated system 10 may have a flow ratio of less than or equal to 1/2, where the flow ratio is the mass flow rate of the portion of the FCDh effluent passed to the separation system divided by the mass flow rate of a portion of the hydrogenation feed contributed by the cracked gas.

In some embodiments, operating the steam cracking system 20 under conditions that increase CO production such that the concentration of CO in the cracked gas 28 is great enough that when the flowrate of the FCDh effluent 34 is zero, the CO concentration in the hydrogenation feed 42 is at least 100 ppmv may reduce or prevent thermal runaway of the acetylene hydrogenation unit 50 in response to a disruption in the flow of the FCDh effluent 34 to the acetylene hydrogenation unit 50. In some embodiments, the steam cracking system 20 may be operated under conditions that increase CO production such that a concentration of CO in the cracked gas 28 is great enough that when a flowrate of the FCDh effluent 34 is zero, a CO concentration in the hydrogenation feed 42 may be from 100 ppmv to 450 ppmv.

In some embodiments, maintaining the amount of the cracker CO in the hydrogenation feed 42 greater than or equal to 20% by mass of the total CO in the hydrogenation feed 42 may reduce or prevent thermal runaway of the acetylene hydrogenation unit 50 in response to a disruption in flow of the FCDh effluent 34 to the acetylene hydrogenation unit 50. A flow ratio of the integrated system may be less than or equal to 1/2, wherein the flow ratio is the mass flow rate of the portion of the FCDh effluent 34 passed to the separation system divided by the mass flow rate of the portion of the cracked gas 28 in the hydrogenation feed 42. As previously discussed, in some embodiments, the steam cracking system 20 may be operated under conditions that increase CO production by modifying an amount of the sulfur-containing compounds 24, methanol 26, or both, introduced to the steam cracking system 20. In some embodiments, the sulfur-containing compounds may include at least one of dimethyl disulfide (DMDS), dimethyl sulfide (DMS), diethyl disulfide (DEDS), methyl mercaptan (MM), or combinations thereof.

Any of the methods disclosed herein may further include operating the acetylene hydrogenation unit 50 at an increased temperature of the hydrogenation feed 42 sufficient to maintain the acetylene concentration in the hydrogenated effluent 52 less than the threshold acetylene concentration at the elevated CO concentration in the hydrogenation feed 42. In some embodiments, the method may include increasing the temperature of the hydrogenation feed 42 in response to increasing an amount of CO in the cracked gas 28 to maintain a concentration of acetylene in the hydrogenated effluent 52 less than the target acetylene concentration. In some embodiments, the target acetylene concentration may be 2 ppmv such that the concentration of acetylene in the hydrogenated effluent 52 is less than or equal to 2 ppmv, or even less than or equal to 1 ppmv.

In some embodiments, the acetylene hydrogenation unit 50 may include at least a first hydrogenation reactor 150 and a second hydrogenation reactor 160 downstream of the first hydrogenation reactor 150. The amount of the cracker CO in the hydrogenation feed 42 of at least 20% by mass of the total CO in the hydrogenation feed 42 may maintain a loss in overall ethylene selectivity in acetylene conversion unit 50 less than or equal to 80% in response to a decrease in the flow of the FCDh effluent 34 to the separation system 40. In some embodiments, in response to a decrease in flow of the at least a portion of the FCDh effluent 34 to the separation system 40, an absolute value of a change in a Delta T of a first hydrogenation reactor 150 of the acetylene hydrogenation unit 50 may be less than 10° C., where the Delta T of the first hydrogenation reactor 150 is a difference between an inlet temperature and an outlet temperature of the first hydrogenation reactor 150.

EXAMPLES

Embodiments of the present disclosure will be further clarified by the following examples, which should not be construed as limiting on the disclosed and/or claimed embodiments presently described.

Example 1: Production and Analysis of FCDh Effluent

In Example 1, an FCDh effluent was produced and analyzed for composition with respect to C3+ compounds and C3− compounds. The propane dehydrogenation was carried out in a modified Davison Circulating Riser (DCR) pilot unit, in which in-situ fuel combustion is carried out in the regeneration section. Approximately 4100 grams of a supported Ga—Pt catalyst was loaded in the circulating system and about 90 g of the catalyst was calculated to be in the reactor at any given time. The inlet temperature to the riser (reactor) was controlled at 630° C. and the pressure was set to a gauge pressure of 90 kilopascals (kPa) (13 psig or absolute pressure of 191 kPa/27.7 psia). High purity propane was injected into the system to achieve a weight hourly space velocity (WHSV) of propane around 3.5 per hour. Nitrogen ($N_2$) was co-fed into the system mostly as a carrier gas of catalyst. The partial pressure of propane was around a gauge pressure of about 30 kPa (4.3 psig). The temperature for catalyst regeneration ranged between 700° C. and 750° C. For Example 1, high purity methane ($CH_4$) was used as the fuel gas in the regenerator and was injected at rate of 50 standard liters per hour.

The reactor system was operated for a period of time sufficient to attain steady state operation, at which point samples of the FCDh effluent from the reactor system were collected and analyzed for composition using techniques known in the art. In particular, the FCDh effluents were analyzed to determine the concentrations of CO, carbon dioxide ($CO_2$), $C_2$ and $C_{2-}$ compounds (including hydrogen), and $C_3$ compounds. The results are provided below in Table 1.

TABLE 1

| Composition of FCDh Effluent of Example 1 | |
|---|---|
| Fuel Gas in Regenerator | High-purity $CH_4$ |
| CO (ppmv) | 1178 |
| $CO_2$ (ppmv) | 88 |
| $C_2$, $C_{2-}$, & $H_2$ (mol %) | 30.6 |
| $C_3$ (mol %) | 69.3 |

The data shows that the concentration of CO in the FCDh effluent can be much greater than the concentration of CO in a typical hydrogenation feed to the acetylene hydrogenation unit, the hydrogenation feed comprising only the cracked gas from a steam cracking system. The typical concentrations for CO in the hydrogenation feed when only the cracked gas is introduced to the separator is provided in Table 2 for a front end de-ethanizer (FEDE) configuration and a front end de-propanizer (FEDP) configuration. Additionally, the concentration of acetylene in the FCDh effluent is less than 50 ppmv. This concentration of acetylene was, therefore, found to be orders of magnitude less than the concentration of acetylene in the feed stream to acetylene converter in a steam cracking system without integration of the FCDh system. The following Table 2 provides the typical concentrations of acetylene the hydrogenation feed when only the cracked gas is introduced to the separator. Table 2 provides data for a front end de-ethanizer (FEDE) and a front end de-propanizer (FEDP) configuration.

TABLE 2

| Comparison of Compositions of the Hydrogenation Feed for FEDE and FEDP Configurations | | |
|---|---|---|
| Configuration | CO in Hydrogenation Feed (ppmv) | Acetylene in Hydrogenation Feed (ppmv) |
| FEDE | 50-200 | 1500-3000 |
| FEDP | 50-400 | 2000-5000 |

Example 2: Modeling of Acetylene Hydrogenation Unit for Integration of FCDh and Steam Cracking An empirical model well practiced for acetylene hydrogenation units is used for evaluating changes in the Delta T of the first hydrogenation reactor and changes in the overall ethylene selectivity of the acetylene hydrogenation unit that occur upon a sudden loss of FCDh stream from an integrated FCDh and Steam Cracking System in which where a portion of cracked gas and a portion of the FCDh effluent are combined and separated with the hydrogenation feed fraction fed to the acetylene hydrogenation unit 50. The sudden loss of the FCDh stream to the integrated FCDh/steam cracking system can be simulated by comparing the Delta T of the first hydrogenation reactor and overall ethylene selectivity of the hydrogenation unit for the combined hydrogenation feed (e.g., the C3/C3− portion of the FCDh effluent and the C3/C3− portion of the cracked gas) to the Delta T of the first hydrogenation reactor and overall ethylene selectivity of the hydrogenation unit for a hydrogenation feed that includes only the portions from the cracked gas (e.g., the C3/C3− portion of the cracked gas). In Example 2, the separation system and acetylene hydrogenation unit have an FEDP configuration. In the FEDP configuration, the hydrogenation feed includes the C3/C3− portion of the cracked gas and the FCDh effluent. The C3/C3− portion of the cracked gas represents the portion of the cracked gas that ends up in the hydrogenation feed when the separation system and acetylene hydrogenation unit have an FEDP configuration. Investigations are carried out with respect to variations in the ratio of the FCDh effluent to the C3/C3− portion of the cracked gas, the CO level in the C3/C3− portion of the cracked gas, the conversion split among the individual acetylene hydrogenation reactors of the acetylene hydrogenation unit, and separation system configuration. In the empirical model, the CO concentration in the FCDh effluent is set at 1200 ppmv for convenience. The concentration of acetylene in the FCDh effluent is not included due to the low concentration compared to the acetylene from the cracked gas and, therefore, the low impact of the acetylene from the FCDh effluent in the modeling.

The acetylene hydrogenation unit used in the model has a configuration of three hydrogenation reactors (A, B, C) in series, each of the hydrogenation reactors having equivalent reactor dimensions, which are typical for an front end depropanizer (FEDP) process configuration. Reactor A (first hydrogenation reactor) carries out the majority of the acetylene conversion, and Reactor B finishes the rest of the conversion. Reactor C is in general a polishing bed to prevent the hydrogenated effluent from being out-of-specification for acetylene concentration. The threshold acetylene concentration in the hydrogenated effluent is set to be less than 1 ppmv. The acetylene conversion splits among Reactor A, B, C are set at targeted values. The composition for the C3/C3− portion of the cracked gas from the steam cracker system used in the model for Examples 2-4 is provided below in Table 3.

TABLE 3

Composition of C3/C3− Portion of the Cracked Gas for Examples 2-4

| Feed Component | Concentration |
|---|---|
| Hydrogen (mol %) | 20 |
| CO (ppmv) | Variable* |
| $CO_2$ (mol %) | 0 |
| $CH_4$ (mol %) | 30.3 |
| Acetylene (ppmv) | 3000 |
| Ethylene ($C_2H_4$) (mol %) | 32.6 |
| Ethane ($C_2H_6$) (mol %) | 5.8 |
| Propylene ($C_3H_6$) (mol %) | 7.5 |
| Propane ($C_3H_8$) (mol %) | 3.5 |
| C4+ Compounds (mol %)** | 0 |

*The concentration of CO in the cracked gas is varied from 50 ppmv to 330 ppmv in Examples 2 through 4.
**Constituents having 4 or more carbon atoms.

The overall GHSV for acetylene hydrogenation unit is 5000 $hr^{-1}$ without the FCDh effluent. The composition for the FCDh effluent in Example 1 is used as the composition for the FCDh effluent in the model prediction.

The modeling is first carried out with the hydrogenation feed that includes both the C3/C3− portion of the cracked gas of Table 3 and the FCDh effluent from Table 1. In Example 2, the concentration of CO in the cracked gas is varied from 50 ppmv to 330 ppmv. The inlet temperature of Reactor A is calculated to reach the targeted acetylene conversion in Reactor A. The inlet temperatures for Reactor B and Reactor C are set at 2° C. less than the inlet temperature for Reactor A. The Delta T for each of Reactors A, B, and C and the overall selectivity to ethylene of the acetylene hydrogenation unit are calculated at steady state conditions. With the acetylene hydrogenation unit operating at steady state, the acetylene hydrogenation unit is subjected to an FCDh system trip, which is simulated by reducing the flow rate of the FCDh effluent to zero. After FCDh trip and reduction of the flow of the FCDh effluent to zero, the inlet temperatures for Reactors A, B, and C remain the same as the temperatures derived for steady state operation with the combined hydrogenation feed (cracked gas and FCDh effluent). The Delta T for each of Reactors A, B, and C and the overall selectivity to ethylene for the acetylene hydrogenation unit is then calculated for after unit trip of the FCDh system.

For Example 2, the acetylene conversion split between Reactors A, B, and C is set to 90:10:0 (90% acetylene conversion for Reactor A, 10% acetylene conversion for Reactor B; the Reactor C is used as polish bed). The flow rate of cracked gas remains constant and the flow ratio is decreased from 1/1 to 1/2, to 1/4, to 1/12. The flow ratio is the mass flow rate of the FCDh effluent divided by the mass flow rate of the C3/C3− portion of the cracked gas (i.e., the portion of the cracked gas that ends up in the hydrogenation feed). The flow ratio, flow rate of the C3/C3− portion of the cracked gas, CO concentration in the C3/C3− portion of the cracked gas, FCDh effluent flow rate, flow rate of the hydrogenation feed, total CO concentration in the hydrogenation feed, change in Delta T for Reactor A (first hydrogenation reactor) resulting from unit trip, the change in overall ethylene selectivity resulting from unit trip, and the amount of CO contributed by the cracked gas as a percentage of the total CO in the hydrogenation feed for Example 2 are provided below in Table 4.

TABLE 4

Modeling Data for Example 2 - Acetylene Conversion Split 90:10:0

| | C3/C3− Portion of Cracked Gas | | FCDh Effluent | | Hydrogenation Feed | | | Change During FCDh unit trip | |
|---|---|---|---|---|---|---|---|---|---|
| | | | | | | | | Increase | Change in |
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | in ΔT − Reactor A (° C.) | overall $C_2H_4$ Selectivity (%) |
| 1/1 | 270 | 50 | 270 | 1200 | 540 | 511 | 6 | 418 | — |
| 1/1 | 270 | 100 | 270 | 1200 | 540 | 541 | 11 | 28 | −381 |
| 1/1 | 270 | 150 | 270 | 1200 | 540 | 571 | 16 | 20 | −247% |
| 1/1 | 270 | 200 | 270 | 1200 | 540 | 601 | 20 | 17 | −188% |
| 1/2 | 270 | 50 | 135 | 1200 | 405 | 338 | 11 | 18 | −245% |
| 1/2 | 270 | 100 | 135 | 1200 | 405 | 375 | 20 | 12 | −137% |
| 1/2 | 270 | 150 | 135 | 1200 | 405 | 413 | 27 | 10 | −98% |

TABLE 4-continued

Modeling Data for Example 2 - Acetylene Conversion Split 90:10:0

| | C3/C3− Portion of Cracked Gas | | FCDh Effluent | | Hydrogenation Feed | | | Change During FCDh unit trip | |
|---|---|---|---|---|---|---|---|---|---|
| | | | | | | | | Increase | Change in |
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | in ΔT − Reactor A (° C.) | overall $C_2H_4$ Selectivity (%) |
| 1/2 | 270 | 200 | 135 | 1200 | 405 | 450 | 33 | 9 | −78% |
| 1/4 | 270 | 50 | 67.5 | 1200 | 337.5 | 215 | 20 | 8 | −99% |
| 1/4 | 270 | 100 | 67.5 | 1200 | 337.5 | 257 | 33 | 6 | −59% |
| 1/4 | 270 | 150 | 67.5 | 1200 | 337.5 | 300 | 43 | 6 | −43% |
| 1/4 | 270 | 200 | 67.5 | 1200 | 337.5 | 343 | 50 | 5 | −35% |
| 1/4 | 270 | 270 | 67.5 | 1200 | 337.5 | 403 | 57 | 5 | −27% |
| 1/4 | 270 | 330 | 67.5 | 1200 | 337.5 | 455 | 62 | 5 | −24% |
| 1/12 | 270 | 50 | 22.5 | 1200 | 292.5 | 111 | 43 | 3 | −29% |
| 1/12 | 270 | 100 | 22.5 | 1200 | 292.5 | 158 | 60 | 3 | −18% |
| 1/12 | 270 | 150 | 22.5 | 1200 | 292.5 | 205 | 69 | 2 | −13% |
| 1/12 | 270 | 200 | 22.5 | 1200 | 292.5 | 253 | 75 | 2 | −10% |

In Table 4, ΔT refers to the Delta T of the Reactor A, which is the difference in temperature between the outlet and the inlet of Reactor A (first hydrogenation reactor). For an increase in Delta T greater than about 10° C., there is a high probability of thermal runaway of the acetylene hydrogenation unit. As shown in Table 4, when the amount of CO from the cracked gas is less than about 20% of the total CO in the hydrogenation feed, such as when the flow ratio is greater than 1/2, the FCDh system may be too large relative to the steam cracking unit, which may make it difficult to compensate for loss of the FCDh effluent to avoid thermal runaway of the hydrogenation unit. Therefore, for flow ratios greater than about 1/2, the FCDh system may be separated from the integrated system and operated as a stand-alone system to reduce or prevent thermal runaway of the hydrogenation unit.

For flow ratio's less than or equal to 1/2, Table 4 indicates that maintaining the concentration of CO in the C3 and C3− portion of the cracked gas greater than or equal to 100 ppmv, greater than or equal to 150 ppmv, or greater than or equal to 200 ppmv based on the total volume of the C3 and C3− portion of the cracked gas and maintaining the amount of CO from the cracked gas greater than 20% of the total CO in the hydrogenation feed may provide for safe operation of the integrated system to reduce or prevent thermal runaway of the acetylene hydrogenation unit in the event the flow rate of the FCDh effluent is reduced to zero.

Example 3: Modeling of Acetylene Hydrogenation Unit for Integration of FCDh and Steam Cracking—Acetylene Conversion Split 95:5:0

For Example 3, the operation of the acetylene hydrogenation unit is modeled based on the separation system and acetylene hydrogenation unit having an FEDP configuration and an acetylene conversion split between the Reactor A, Reactor B, and Reactor C of 95:5:0, which may be a more conservative approach to operation in order to decrease the probability of producing out of specification product streams having an acetylene concentration in the hydrogenated effluent greater than the threshold acetylene concentration. The modeling is performed according to the method of Example 2 except that the acetylene conversion split between Reactor A, Reactor B, and Reactor C is set at 95:5:0. All other variables and assumptions are the same as in Example 2. The modeling results for Example 3 are provided below in Table 5.

TABLE 5

Modeling Data for Example 3 - Acetylene Conversion Split 95:5:0

| | C3/C3− Portion of Cracked Gas | | FCDh Effluent | | Hydrogenation Feed | | | Change During FCDh unit trip | |
|---|---|---|---|---|---|---|---|---|---|
| | | | | | | | | Increase | Change in |
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | in ΔT − Reactor A (° C.) | Overall $C_2H_4$ Selectivity (%) |
| 1/2 | 270 | 50 | 135 | 1200 | 405 | 338 | 11 | 26 | −382 |
| 1/2 | 270 | 100 | 135 | 1200 | 405 | 375 | 20 | 15 | −194 |
| 1/2 | 270 | 150 | 135 | 1200 | 405 | 413 | 27 | 12 | −136 |
| 1/2 | 270 | 200 | 135 | 1200 | 405 | 450 | 33 | 11 | −107 |
| 1/4 | 270 | 50 | 67.5 | 1200 | 337.5 | 215 | 20 | 11 | −138 |
| 1/4 | 270 | 100 | 67.5 | 1200 | 337.5 | 257 | 33 | 7 | −81 |
| 1/4 | 270 | 150 | 67.5 | 1200 | 337.5 | 300 | 43 | 6 | −59 |
| 1/4 | 270 | 200 | 67.5 | 1200 | 337.5 | 343 | 50 | 6 | −47 |
| 1/4 | 270 | 270 | 67.5 | 1200 | 337.5 | 403 | 57 | 5 | −37 |
| 1/4 | 270 | 330 | 67.5 | 1200 | 337.5 | 455 | 62 | 5 | −32 |
| 1/12 | 270 | 50 | 22.5 | 1200 | 292.5 | 111 | 43 | 3 | −39 |

TABLE 5-continued

Modeling Data for Example 3 - Acetylene Conversion Split 95:5:0

| | C3/C3− Portion of Cracked Gas | | FCDh Effluent | | Hydrogenation Feed | | | Change During FCDh unit trip | |
|---|---|---|---|---|---|---|---|---|---|
| | | | | | | | | Increase | Change in |
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | in ΔT − Reactor A (° C.) | Overall $C_2H_4$ Selectivity (%) |
| 1/12 | 270 | 100 | 22.5 | 1200 | 292.5 | 158 | 60 | 3 | −24 |
| 1/12 | 270 | 150 | 22.5 | 1200 | 292.5 | 205 | 69 | 2 | −17 |
| 1/12 | 270 | 200 | 22.5 | 1200 | 292.5 | 253 | 75 | 2 | −14 |

Comparing Table 5 to Table 4, increasing the acetylene conversion split from 90:10:0 in Example 2 to 95:5:0 in Example 3 may increase the magnitude in the change in Delta T in Reactor A and change in the ethylene selectivity of the hydrogenation unit. When the acetylene conversion split is increased, the steam cracking unit may need to be operated to further increase the amount of CO produced in the cracked gas to further compensate for the CO in the FCDh effluent in the event the flow rate of the FCDh effluent decreases to zero. As shown in Table 5, when the acetylene conversion split is increased to 95:5:0, at a flow ratio of 1/2, the concentration of CO in the C3 and C3− portion of the cracked gas may be maintained at greater than or equal to 150 to maintain safe operation of the acetylene hydrogenation unit.

Example 4: Modeling of Acetylene Hydrogenation Unit for Integration of FCDh and Steam Cracking—Acetylene Conversion Split 99:1:0

For Example 4, the operation of the acetylene hydrogenation unit is modeled based on the separation system and acetylene hydrogenation unit having an FEDP configuration and an acetylene conversion split between the Reactor A, Reactor B, and Reactor C of 99:1:0. The modeling is performed according to the method of Example 2 except that the acetylene conversion split between Reactor A, Reactor B, and Reactor C is set at 99:1:0. All other variables and assumptions are the same as in Example 2. The modeling results for Example 4 are provided below in Table 6.

As shown in Table 6, when the acetylene conversion split is further increased from 95:5:0 in Example 3 to 99:1:0 in Example 4, the magnitude in Delta T for Reactor A and change in the ethylene selectivity are even further increased. Thus, when the acetylene conversion split is increased to 99:1:0, a flow ratio of 1/2 may lead to an increased probability of thermal runaway in the event of a reduction in the flowrate of the FCDh effluent to zero, and increasing the CO produced in the steam cracking unit may not be sufficient to compensate for the loss of the FCDh system. Examples 3 and 4 demonstrate that increasing the acetylene conversion in the Reactor A (first hydrogenation reactor) in order to ensure the concentration of acetylene in the hydrogenated feed is less than the threshold acetylene concentration may result in increasing the probability of thermal runaway. However, this probability of thermal runaway can be decreased by increasing the amount of CO in the cracked gas.

Example 5: Modeling of Acetylene Hydrogenation Unit for Integration of FCDh and Steam Cracking Having an FEDE Configuration In Example 5, the separation system and acetylene hydrogenation unit have an FEDE configuration. In the FEDE configuration, the hydrogenation feed includes the C2/C2− portion of the cracked gas and the C2/C2− portion of the FCDh effluent. The C2/C2− portion of the cracked gas and the C2/C2− portion of the FCDh effluent represent the portions of the cracked gas and FCDh effluent, respectively,

TABLE 6

Modeling Data for Example 4 - Acetylene Conversion Split 99:1:0

| | C3/C3− Portion of Cracked Gas | | FCDh Effluent | | Hydrogenation Feed | | | Change During FCDh unit trip | |
|---|---|---|---|---|---|---|---|---|---|
| | | | | | | | | Increase | Change in |
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | in ΔT − Reactor A (° C.) | Overall $C_2H_4$ Selectivity (%) |
| 1/4 | 270 | 50 | 67.5 | 1200 | 337.5 | 215 | 20 | 17 | −253 |
| 1/4 | 270 | 100 | 67.5 | 1200 | 337.5 | 257 | 33 | 11 | −137 |
| 1/4 | 270 | 150 | 67.5 | 1200 | 337.5 | 300 | 43 | 9 | −99 |
| 1/4 | 270 | 200 | 67.5 | 1200 | 337.5 | 343 | 50 | 8 | −78 |
| 1/4 | 270 | 270 | 67.5 | 1200 | 337.5 | 403 | 57 | 7 | −61 |
| 1/4 | 270 | 330 | 67.5 | 1200 | 337.5 | 455 | 62 | 6 | −54 |
| 1/12 | 270 | 50 | 22.5 | 1200 | 292.5 | 111 | 43 | 4 | −50 |
| 1/12 | 270 | 100 | 22.5 | 1200 | 292.5 | 158 | 60 | 3 | −28 |
| 1/12 | 270 | 150 | 22.5 | 1200 | 292.5 | 205 | 69 | 2 | −18 |
| 1/12 | 270 | 200 | 22.5 | 1200 | 292.5 | 253 | 75 | 2 | −14 | that ends up in the hydrogenation feed when the separation system and acetylene hydrogenation unit have an FEDE configuration. Investigations are carried out with respect to variations in the ratio of the FCDh effluent to the C2/C2− portion of the cracked gas (flow ratio), the CO level in the C2/C2− portion of the cracked gas, and the conversion split among the individual acetylene hydrogenation reactors of the acetylene hydrogenation unit. In the empirical model for Example 5, the CO concentration in the FCDh effluent is set at 1200 ppmv for convenience. The concentration of acetylene in the FCDh effluent is not included due to the low concentration compared to the acetylene from the cracked gas.

The acetylene hydrogenation unit used in the model has a configuration of two hydrogenation reactors (A and B) in series, each of the two hydrogenation reactors having equivalent reactor dimensions, which are typical for an FEDE process configuration. Reactor A (first hydrogenation reactor) carries out the majority of the acetylene conversion, and Reactor B finishes the rest of the conversion. The conversion split between reactor A and reactor B in example 5 is 99:1. The threshold acetylene concentration in the hydrogenated effluent is set to be less than 1 ppmv. The composition for the C2/C2− portion of the cracked gas from the steam cracker system used in the model for Example 5 is provided below in Table 7.

TABLE 7

Composition of C2/C2− Portion of the Cracked Gas for Example 5

| Feed Component | Concentration |
|---|---|
| Hydrogen (mol %) | 30.3 |
| CO (ppmv) | Variable* |
| $CO_2$ (mol %) | 0.0 |
| $CH_4$ (mol %) | 9.0 |
| Acetylene (ppmv) | 2300 |
| Ethylene ($C_2H_4$) (mol %) | 42.0 |
| Ethane ($C_2H_6$) (mol %) | 18.5 |

*The concentration of CO in the C2/C2− Portion of the cracked gas is varied from 50 ppmv to 200 ppmv in Example 5.

The overall GHSV for acetylene hydrogenation unit is 7000 $hr^{-1}$ without the FCDh effluent. The composition for the FCDh effluent of Example 1 without the C3 compounds (only the CO, $CO_2$, C2, C2−, and $H_2$ components) is used as the composition for the FCDh effluent in the model prediction for Example 5.

The modeling is first carried out with the hydrogenation feed that includes both the C2/C2− portion of the cracked gas of Table 7 and the C2/C2− portions of the FCDh effluent from Table 1. In Example 5, the concentration of CO in the cracked gas is varied from 50 ppmv to 330 ppmv. The inlet temperature of Reactor A is calculated to reach the targeted acetylene conversion in Reactor A. The inlet temperature for Reactor B is set at 2° C. less than the inlet temperature for Reactor A. The Delta T for each of Reactors A and B and the overall selectivity to ethylene of the acetylene hydrogenation unit are calculated at steady state conditions. With the acetylene hydrogenation unit operating at steady state, the acetylene hydrogenation unit is subjected to an FCDh system trip, which is simulated by reducing the flow rate of the FCDh effluent to zero. After FCDh trip and reduction of the flow of the FCDh effluent to zero, the inlet temperatures for Reactors A and B are held constant at the temperatures derived for steady state operation with the combined hydrogenation feed (cracked gas and FCDh effluent). The Delta T for each of Reactors A and B and the overall selectivity to ethylene for the acetylene hydrogenation unit is then calculated after unit trip of the FCDh system.

For Example 5, the acetylene conversion split between Reactors A and B is set to 99:1 (99% acetylene conversion for Reactor A, 1% acetylene conversion for Reactor B) in order to ensure sufficient conversion of acetylene in the acetylene hydrogenation unit to provide a concentration of acetylene in the hydrogenated feed less than the threshold acetylene concentration. The flow rate of cracked gas remains constant and the flow ratio is decreased from 1/1 to 1/3, to 1/6, to 1/12. The flow ratio is the mass flow rate of the FCDh effluent (all of the FCDh effluent and not just the C2/C2− portion) divided by the mass flow rate of the C2/C2− portion of the cracked gas (i.e., the portion of the cracked gas that ends up in the hydrogenation feed). The results of the modeling for Example 5 are provided below in Table 8.

TABLE 8

Modeling Data for Example 5 - Acetylene Conversion Split 99:1 and FEDE Configuration

| | C2/C2− Portion of Cracked Gas | | FCDh Effluent | | Hydrogenation Feed | | | Change During FCDh unit trip | |
|---|---|---|---|---|---|---|---|---|---|
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | Increase in ΔT − Reactor A (° C.) | Change in Overall $C_2H_4$ Selectivity (%) |
| 1/1 | 270 | 50 | 270 | 1200 | 281 | 657 | 6 | 109.7 | — |
| 1/1 | 270 | 100 | 270 | 1200 | 281 | 699 | 11 | 16 | −276 |
| 1/1 | 270 | 150 | 270 | 1200 | 281 | 741 | 16 | 10 | −173 |
| 1/1 | 270 | 200 | 270 | 1200 | 281 | 783 | 20 | 7.3 | −128 |
| 1/3 | 270 | 50 | 90 | 1200 | 274 | 276 | 16 | 9.5 | −162 |
| 1/3 | 270 | 100 | 90 | 1200 | 274 | 323 | 27 | 5.1 | −88 |
| 1/3 | 270 | 150 | 90 | 1200 | 274 | 370 | 36 | 3.5 | −61 |
| 1/3 | 270 | 200 | 90 | 1200 | 274 | 417 | 43 | 2.7 | −47 |
| 1/6 | 270 | 50 | 45 | 1200 | 272 | 167 | 27 | 4.5 | −78 |
| 1/6 | 270 | 100 | 45 | 1200 | 272 | 215 | 43 | 2.2 | −45 |
| 1/6 | 270 | 150 | 45 | 1200 | 272 | 264 | 53 | 1.9 | −32 |
| 1/6 | 270 | 200 | 45 | 1200 | 272 | 312 | 60 | 1.4 | −25 |
| 1/12 | 270 | 50 | 22.5 | 1200 | 271 | 109 | 43 | 2.0 | −39 |
| 1/12 | 270 | 100 | 22.5 | 1200 | 271 | 158 | 60 | 1.3 | −24 |

TABLE 8-continued

Modeling Data for Example 5 - Acetylene Conversion Split 99:1 and FEDE Configuration

| | C2/C2− Portion of Cracked Gas | | FCDh Effluent | | Hydrogenation Feed | | | Change During FCDh unit trip | |
|---|---|---|---|---|---|---|---|---|---|
| | | | | | | | | Increase | Change in |
| Flow Ratio | Flow Rate (ton/hr) | CO Conc. (ppmv) | Flow Rate (ton/hr) | CO Conc. (ppmv) | Flow Rate (ton/hr) | Total CO (ppmv) | % CO from Cracker | in ΔT − Reactor A (° C.) | Overall C$_2$H$_4$ Selectivity (%) |
| 1/12 | 270 | 150 | 22.5 | 1200 | 271 | 208 | 69 | 1.0 | −18 |
| 1/12 | 270 | 200 | 22.5 | 1200 | 271 | 257 | 75 | 0.7 | −14 |

As shown in Table 8, for the two reactor FEDE acetylene hydrogenation unit configuration, when the flow ratio is 1/1, increasing the amount of CO in the cracked gas so that the concentration of CO from the cracked gas in the hydrogenation feed is at least 20% may not be sufficient to avoid thermal runaway of the acetylene hydrogenation unit. Therefore, for flow ratios of 1/1, the FCDh system may be operated as a stand-alone system without integrated the FCDh effluent into the separation system 40. Referring again to Table 8, for a flow ratio of 1/3, increasing the amount of CO in the cracked gas so that, when a flowrate of the FCDh effluent is zero, a CO concentration in the hydrogenation feed is at least 100 ppmv (i.e., the concentration of CO in the C3/C3− portion of the cracked gas) may reduce the change in Delta T to less than 6, which may provide safer operation of the acetylene hydrogenation unit by reducing or preventing thermal runaway of the acetylene hydrogenation unit.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the process 10 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the process 10 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for operating an acetylene hydrogenation unit in an integrated steam cracking-fluidized catalytic dehydrogenation (FCDh) system, the method comprising:
    cracking at least a portion of a first hydrocarbon feed in a steam cracking system to produce a cracked gas comprising at least hydrogen, carbon monoxide (CO), and acetylene;
    dehydrogenating at least a portion of a second hydrocarbon feed in an FCDh system to produce an FCDh effluent comprising at least hydrogen and CO;
    separating the cracked gas and at least a portion of the FCDh effluent into a hydrogenation feed and an acetylene-depleted stream, the hydrogenation feed comprising at least hydrogen, CO, and acetylene, wherein the hydrogenation feed comprises at least 95% of the CO from the cracked gas and the FCDh effluent, and wherein during normal operating conditions at least 20% of the CO in the hydrogenation feed is from the cracked gas, wherein during normal operating conditions, both the steam cracking system and the FCDh system are operating at high temperatures and steady state;
    contacting the hydrogenation feed with an acetylene hydrogenation catalyst in an acetylene hydrogenation unit, the contacting causing hydrogenation of at least a portion of the acetylene in the hydrogenation feed to produce a hydrogenated effluent; and
    operating the steam cracking system under conditions that produce a CO concentration in the hydrogenation feed of at least 100 ppmv when a flowrate of the FCDh effluent is zero.

2. The method of claim 1, wherein operating the steam cracking system under conditions that produce a CO concentration in the hydrogenation feed of at least 100 ppmv when a flowrate of the FCDh effluent is zero reduces or prevents thermal runaway of the acetylene hydrogenation unit in response to the flowrate of zero of the FCDh effluent to the acetylene hydrogenation unit.

3. The method of claim 1, wherein the CO concentration in the hydrogenation feed is from 100 ppmv to 450 ppmv when the flowrate of the FCDh effluent is zero.

4. The method claim 1, wherein maintaining the amount of the CO from the cracked gas in the hydrogenation feed greater than or equal to 20% by mass of the total amount of CO in the hydrogenation feed reduces or prevents thermal runaway of the acetylene hydrogenation unit in response to a disruption in flow of the FCDh effluent to the acetylene hydrogenation unit.

5. The method of claim 1, wherein the steam cracking system is operated to increase CO production by decreasing an amount of sulfur-containing compounds introduced to the steam cracking system.

6. The method of claim 5, wherein the sulfur-containing compounds comprise at least one of dimethyl disulfide (DMDS), dimethyl sulfide (DMS), diethyl disulfide (DEDS), methyl mercaptan (MM), or combinations thereof.

7. The method of claim 1, further comprising increasing a temperature of the hydrogenation feed in response to increasing an amount of CO in the cracked gas to maintain a concentration of acetylene in the hydrogenated effluent less than a threshold acetylene concentration.

8. The method of claim 1, wherein the acetylene hydrogenation unit comprises at least a first hydrogenation reactor and a second hydrogenation reactor downstream of the first hydrogenation reactor, and wherein the amount of CO from the cracked gas in the hydrogenation feed is greater than or equal to 20% of the total amount of CO in the hydrogenation feed, the flowrate of the FCDh effluent to the acetylene hydrogenation unit is decreased, and an overall ethylene selectivity is reduced by less than or equal to 80% in response to the decrease in the flowrate of the FCDh effluent to the acetylene hydrogenation unit.

9. The method of claim 1, in which in response to a decrease in flow of the at least a portion of the FCDh effluent to the separator, an absolute value of a change in a Delta T of a first hydrogenation reactor of the acetylene hydrogenation unit is less than 10° C., wherein the Delta T of the first hydrogenation reactor is a difference between an inlet temperature and an outlet temperature of the first hydrogenation reactor.

10. The method of claim 1, wherein a flow ratio is less than or equal to 1/2, wherein the flow ratio is the mass flow rate of the portion of the FCDh effluent passed to the separation system divided by the mass flow rate of the portion of the cracked gas in the hydrogenation feed.

11. The method of claim 1, wherein the hydrogenation feed comprises methyl acetylene, propadiene, and at least one cracker product, the at least one cracker product comprising one or more of ethylene, propylene, methane, ethane, propane, or combinations of these.

12. The method of claim 1, wherein the hydrogenated effluent has a concentration of acetylene of less than or equal to 2 ppm by volume.

13. The method of claim 1, wherein the FCDh effluent comprises at least one FCDh product, wherein the at least one FCDh product comprises ethylene, propylene, or both.

14. The method of claim 1, wherein during normal operating conditions the steam cracking system is operated at a temperature of greater than 550° C.

15. The method of claim 1, wherein during normal operating conditions the FCDh system is operated at a temperature of greater than 550° C.

* * * * *